(12) United States Patent
McLaughlin et al.

(10) Patent No.: US 12,708,682 B2
(45) **Date of Patent: *Aug. 18, 2026**

(54) IRRADIATION APPARATUS

(71) Applicants: SCINTACOR LIMITED, Cambridge (GB); PRECISION X-RAY, INC., North Branford, CT (US)

(72) Inventors: William McLaughlin, North Branford, CT (US); John Laviola, North Branford, CT (US); Edward Frederick Bullard, Cambridge (GB)

(73) Assignees: SCINTACOR LIMITED, Cambridge (GB); PRECISION X-RAY, INC., North Branford, CT (US)

( * ) Notice: Subject to any disclaimer, the term of this patent is extended or adjusted under 35 U.S.C. 154(b) by 490 days.

This patent is subject to a terminal disclaimer.

(21) Appl. No.: 18/249,604

(22) PCT Filed: Oct. 22, 2021

(86) PCT No.: PCT/US2021/056183
§ 371 (c)(1),
(2) Date: Apr. 19, 2023

(87) PCT Pub. No.: WO2022/087363
PCT Pub. Date: Apr. 28, 2022

(65) Prior Publication Data

US 2023/0390433 A1 Dec. 7, 2023

(30) Foreign Application Priority Data

Oct. 24, 2020 (GB) ..................................... 2016907

(51) Int. Cl.
*G01N 23/04* (2018.01)
*A61L 2/082* (2026.01)
(Continued)

(52) U.S. Cl.
CPC ............ *A61L 2/082* (2013.01); *A61N 5/1084* (2013.01); *A23B 2/50* (2025.01); *A61B 6/4258* (2013.01);
(Continued)

(58) Field of Classification Search
CPC ........... G01N 23/04; G01N 2223/3307; G01N 2223/3308; G01N 2223/643; G01N 23/10;
(Continued)

(56) References Cited

U.S. PATENT DOCUMENTS 2,416,142 A 2/1947 Bennett
4,029,967 A 6/1977 Tetzlaff
(Continued)

FOREIGN PATENT DOCUMENTS

CN 104701119 A 6/2015
CN 104900294 A 9/2015
(Continued)

OTHER PUBLICATIONS

"International Search Report and Written Opinion of the International Searching Authority", International Application No. PCT/US2021/056177, Feb. 2, 2022, 10 pp.
(Continued)

*Primary Examiner* — Wyatt A Stoffa
(74) *Attorney, Agent, or Firm* — Myers Bigel, P.A.

(57) ABSTRACT

An irradiation apparatus comprises a plurality of ionising radiation source points (122) configured to output ionising radiation. The plurality of ionising radiation source points (122) is an array distributed around an irradiation volume (140). The array of ionising radiation source points (122) is configured to direct ionising radiation inwardly to the irradiation volume (140). A transport apparatus (130) is configured to support at least one sample (138) to be irradiated.
(Continued)

The transport apparatus (130) is configured to transport samples along a linear path through the irradiation volume (140).

30 Claims, 13 Drawing Sheets

(51) Int. Cl.
*A61N 5/10* (2006.01)
*A23B 2/50* (2025.01)
*A61B 6/42* (2024.01)
*G01N 23/083* (2018.01)
*G01N 23/10* (2018.01)
*G01V 5/22* (2024.01)

(52) U.S. Cl.
CPC ......... *A61L 2202/14* (2013.01); *A61N 5/1078* (2013.01); *G01N 23/04* (2013.01); *G01N 23/083* (2013.01); *G01N 23/10* (2013.01); *G01V 5/22* (2024.01)

(58) Field of Classification Search
CPC ...... G01N 23/083; G01N 23/095; G01V 5/22; A61B 6/42; A61B 6/4258; A61B 6/4266; A23B 2/503; A23B 2/53; A23B 2/50; A61L 2/082; A61L 2/10; A61L 2/087; A61N 5/1064; A61N 5/1048; A61N 5/1078; A61N 2005/1089; A61N 2005/1091
See application file for complete search history.

(56) References Cited

U.S. PATENT DOCUMENTS 4,093,863 A 6/1978 Zacher
4,289,969 A 9/1981 Cooperstein et al.
5,111,492 A * 5/1992 Klausz .................. A61B 6/481 378/98.2
5,838,760 A * 11/1998 Moses ..................... G21K 5/10 378/66
6,165,526 A * 12/2000 Newman ................ A23B 2/055 426/248
6,225,631 B1 * 5/2001 Mastrippolito ...... A61B 6/4258 250/363.08
6,556,651 B1 4/2003 Thomson et al.
6,713,773 B1 * 3/2004 Lyons ..................... G21K 5/10 378/68
6,735,274 B1 5/2004 Zahavi et al.
6,763,085 B2 * 7/2004 Hansen .................. A23B 2/503 378/69
7,324,630 B2 * 1/2008 Avnery .................... A61L 2/08 378/140
7,415,094 B2 * 8/2008 Johnson .................. G01V 5/22 378/57
7,486,771 B2 * 2/2009 Stichelbaut ............. A61L 2/082 378/69
7,682,641 B1 3/2010 Vasilenko
8,000,436 B2 * 8/2011 Seppi ..................... G01V 5/226 378/57
8,132,598 B2 * 3/2012 Mastio ...................... B67C 3/22 53/425
8,243,876 B2 * 8/2012 Morton ................ G01N 23/046 378/146
8,748,827 B2 * 6/2014 Zilberstein .............. G21K 1/02 250/363.04
8,837,670 B2 * 9/2014 Akery ....................... G01T 1/24 378/57
8,919,280 B1 * 12/2014 Haff ........................ A61D 1/00 119/6.5
9,052,264 B2 * 6/2015 Bendahan ............. G01N 23/04
9,223,050 B2 * 12/2015 Kaval .................... G01N 23/04
9,279,901 B2 * 3/2016 Akery ...................... G01V 5/22
10,175,381 B2 * 1/2019 Morton .................... H05G 1/70
10,295,483 B2 * 5/2019 Morton ..................... G06T 7/12
10,585,206 B2 * 3/2020 Bendahan ................ G01V 5/22
10,806,950 B2 * 10/2020 Fahrig .................. A61N 5/1084
11,055,635 B2 * 7/2021 Sanderson ............. B65G 43/08
11,261,315 B1 * 3/2022 Hosseinnezhad Mohtarami ......... C08J 3/20
11,583,602 B2 2/2023 Cawley
2002/0008213 A1 * 1/2002 Kawada ................ H01J 37/317 250/492.3
2002/0149321 A1 10/2002 Avnery
2002/0154740 A1 10/2002 Avnery
2003/0128807 A1 7/2003 Kotler et al.
2003/0142784 A1 * 7/2003 Suzuki .................. G01N 23/04 378/58
2005/0031077 A1 2/2005 Avnery
2005/0226364 A1 10/2005 Bernard et al.
2006/0049359 A1 3/2006 Busta et al.
2007/0025505 A1 * 2/2007 Bjorkholm ............ G01V 5/224 378/53
2007/0133743 A1 * 6/2007 Johnson ................. B64F 1/368 378/57
2008/0025464 A1 * 1/2008 Foland .................. G01N 23/04 378/57
2008/0205583 A1 8/2008 Seppi et al.
2008/0273661 A1 * 11/2008 Kirk ........................ G21K 5/10 378/69
2009/0067575 A1 3/2009 Seppi et al.
2009/0285353 A1 11/2009 Ellenbogen et al.
2010/0189221 A1 7/2010 Eaton et al.
2011/0020174 A1 1/2011 Rauschnabel et al.
2012/0152885 A1 6/2012 Munoz
2013/0177136 A1 7/2013 Moses et al.
2015/0199804 A1 7/2015 Chen et al.
2017/0118829 A1 4/2017 Hartman et al.
2018/0078790 A1 3/2018 Lee et al.
2018/0299580 A1 10/2018 Morton
2023/0381354 A1 * 11/2023 Mclaughlin ........... A23B 4/044
2026/0101987 A1 * 4/2026 Dijkstra ................ A45D 33/32

FOREIGN PATENT DOCUMENTS

CN 104701119 B 12/2017
CN 110225638 A 9/2019
EP 2412388 A1 2/2012
JP H075100 U 1/1995
JP 2002025493 A 1/2002
JP 2003227900 A 8/2003
WO 2022087357 A1 4/2022

OTHER PUBLICATIONS

"International Search Report and Written Opinion of the International Searching Authority", PCT Application No. PCT/US2021/056183, Mar. 3, 2022, 13 pp.
"Patents Act 1977: Combined Search and Examination Report under Sections 17 and 18(3)", GB Application No. GB2016907.4, Apr. 27, 2021, 6 pp.
"Patents Act 1977: Combined Search and Examination Report under Sections 17 and 18(3)", GB Application No. GB2016906.6, Apr. 27, 2021, 7 pp.
Communication with Supplementary European Search Report, EP Application No. 21883952.0, Feb. 11, 2025, 14 pp.
Communication with Supplementary European Search Report, EP Application No. 21883956.1, Feb. 11, 2025, 19 pp.
Anonymous, "CT scan—Wikipedia", Retrieved from the Internet: URL:https://en.wikipedia.org/w/index.php?title=CT_scan&oldid=984835358, XP093195763, Oct. 22, 2020, 37 pp.

* cited by examiner

120

120
120g

IRRADIATION APPARATUS

RELATED APPLICATIONS

This application is a 35 U.S.C. § 371 national stage application of PCT Application No. PCT/US2021/056183, filed on Oct. 22, 2021, which claims priority from GB Patent Application No. 2016907.4, filed on Oct. 24, 2020, the contents of which are incorporated herein by reference in their entireties. The above-referenced PCT International Application was published in the English language as International Publication No. WO 2022/087363 A1 on Apr. 28, 2022.

BACKGROUND

The treatment of objects and bulk materials using radiation, such as x-rays, is an effective method of treating a variety of objects or materials such as seeds, stem cells, blood, medical devices, tobacco, marijuana and food stuffs. It can also be used with animals and insects. Some useful effects of irradiation are to: destroy or degrade pathogens (e.g. virus, bacteria, mould) or leucocytes; destroy unwanted insects and chemical materials such as pesticides; and delay biological processes such as the ripening of fruit.

The irradiation process for a given application requires a specific uniformity of the distribution of absorbed dose throughout the object being irradiated. A 10% variation of deposited dose throughout the object is typically acceptable, although this varies depending on the application.

Isotopic sources such as Caesium-137 (Cs-137) and Cobalt-60 (Co-60) are commonly used for irradiation. These isotopes emit gamma photons with energies of 662 keV and 1.2 MeV respectively. These relatively high energy photons penetrate well through organic materials such as food stuffs and therefore easily achieve a good dose distribution. However, they have undesirable alternative uses and require large fixed facilities with significant radiation shielding and security. X-ray sources can be used for irradiation. An X-ray source is typically an evacuated sealed tube in which electrons emitted from a tungsten filament (the cathode) are accelerated onto a metal sample (the anode) through the use of electrical voltage. Isotopic sources emit a single wavelength of radiation. In an X-ray source the anode material re-emits the energy received from the electrons as characteristic X-ray emission lines lying on top of Bremsstrahlung radiation spectrum extending from very low energy X-ray photons up to the voltage potential applied between anode and cathode. Because X-ray sources generate this broad Bremsstrahlung spectrum of radiation, the uniformity of absorbed dose they generate is inferior to isotopic sources of the same maximum energy when used for irradiation.

X-ray sources have an advantage of only producing radiation when they are energised, so they present less of a radiological security risk and can be used in mobile systems. Although convenient, the power dissipation of these devices and hence their X-ray output is low. X-ray sources also have lower energy, typically 25 kV to 550 kV, than Cs-137 and Co-60 and this also leads to inferior dose uniformity.

It is an aim of the present invention to address at least one disadvantage associated with the prior art.

SUMMARY OF THE INVENTION

There is provided an irradiation apparatus comprising:

a shielded housing;

a plurality of ionising radiation source points configured to output ionising radiation, wherein the plurality of ionising radiation source points is an array distributed around an irradiation volume and the array of ionising radiation source points is configured to direct ionising radiation inwardly to the irradiation volume, a transport apparatus configured to support at least one sample to be irradiated, wherein the transport apparatus is configured to transport samples along a linear path through the irradiation volume.

An advantage of at least one example or embodiment is a more uniform dose of radiation to samples in the irradiation volume. In use, samples are exposed to radiation which arrives from a range of different directions. The plurality of radiation source points can provide a more uniform dose of radiation.

An advantage of positioning ionising radiation source points around an irradiation volume is that it can allow a much larger anode area where kinetic energy of electrons is converted to radiation. This can allow high energy levels for long periods of time (if required). Typically, an ionising radiation source point (e.g. an anode of an x-ray tube) will convert less than 1% of the kinetic energy of electrons to ionising radiation, with the remainder converted to heat. Dissipating the unwanted heat is a significant problem. Positioning ionising radiation source points around an irradiation volume can also allow easier dissipation of unwanted heat energy.

Optionally, the array of ionising radiation source points comprises a ring of ionising radiation source points. This shape is advantageous as the plurality of source points are equi-distant about a longitudinal axis of the irradiation volume. The ring can be implemented as a ring-shaped single evacuated tube with the plurality of ionising radiation source points distributed around the ring-shaped tube. Alternatively, the plurality of ionising radiation source points can be implemented by individual sources, such as individual x-ray tubes.

Optionally, the array of ionising radiation source points comprise a plurality of rings of ionising radiation source points, wherein the rings are offset along the linear path.

Optionally, the plurality of ionising radiation source points comprise a rectilinear array of ionising radiation source points.

Optionally, the linear path is orthogonal to a plane of the array of ionising radiation source points.

Optionally, the irradiation apparatus comprises a total of N ionising radiation source points, and the irradiation apparatus is configured to simultaneously activate up to N of the ionising radiation source points during an irradiation cycle.

Optionally, the irradiation apparatus is configured to independently control operating parameters of each of the plurality of ionising radiation source points during an irradiation cycle.

Optionally, the operating parameters for an ionising radiation source point are at least one of:

an activation state of the ionising radiation source point;

an operating current and/or an operating voltage of the ionising radiation source point;

a parameter for a beam controlling device of the ionising radiation source point.

Optionally, the plurality of ionising radiation source points comprise at least one of: a plurality of individual ionising radiation sources; an ionising radiation source with a plurality of ionising radiation source points.

Optionally, the irradiation apparatus comprises a detector array and wherein the irradiation apparatus is configured to image the irradiation volume using at least one of the ionising radiation source points and the detector array.

Optionally, the irradiation apparatus comprises a detector array and wherein the irradiation apparatus is configured to image the irradiation volume using at least some of the ionising radiation source points and the detector array.

Optionally, the irradiation apparatus is configured to operate the ionising radiation source points at a first radiation level during imaging and to operate the ionising radiation source points at a second radiation level, higher than the first radiation level, during irradiation. For example, the first radiation level can be a dose of less than 0.1 Gy.

Optionally, the irradiation apparatus is configured to image the irradiation volume by:

activating different ones of the ionising radiation source points to emit a beam of radiation for imaging; and using the detector array to acquire image data.

Optionally, the irradiation apparatus is configured to use the acquired image data to construct a three-dimensional image.

Optionally, the irradiation apparatus is configured to control the plurality of ionising radiation source points based on the acquired image data.

Optionally; the plurality of ionising radiation source points form a first array for irradiation purposes, the irradiation apparatus comprising:

a second array of ionising radiation source points distributed around an imaging volume and a detector array, wherein the irradiation apparatus is configured to image the imaging volume using the radiation source points and the detector array, wherein the irradiation volume is linearly offset from the imaging volume along the linear path.

Optionally, the irradiation apparatus is configured to image the irradiation volume by:

activating different ones of the ionising radiation source points of the second array to emit a beam of radiation for imaging; and using the detector array to acquire image data.

Optionally, the irradiation apparatus is configured to control the plurality of ionising radiation source points of the first array based on the acquired image data.

Optionally, the irradiation apparatus is configured to determine data indicative of density of a sample within the irradiation volume.

Optionally, the irradiation apparatus is configured to determine data indicative of density of a sample within the irradiation volume based on the acquired image data.

Optionally, the irradiation apparatus is configured to determine data indicative of volumetric and/or spatial distribution of a sample within the irradiation volume based on the acquired image data.

Optionally, the irradiation apparatus is configured to determine a required amount of irradiation to which a sample is to be subject based on the acquired image data and to control the plurality of ionising radiation source points to deliver the required amount.

Optionally, the irradiation apparatus is configured to control the plurality of ionising radiation source points to deliver the required amount of radiation to the sample taking into account a reduction in the amount of radiation that reaches the sample due to the presence of a sample holder and/or sample packaging.

Optionally, the irradiation apparatus is configured to determine at least one of:

a number of ionising radiation source points to be activated;

an operating current and/or an operating voltage of each of the activated ionising radiation source points;

a parameter for a beam controlling device at an ionising radiation source point;

a total duration of the irradiation.

Optionally, the transport apparatus comprises a conveyor belt.

Optionally, the irradiation apparatus is configured to vary a speed at which samples are moved along the linear path by the transport apparatus. The irradiation apparatus may be configured to vary the speed based on acquired image data, which is indicative of properties of the sample.

Optionally, the transport apparatus is configured to vary the position of samples during the linear path through the irradiation volume.

Optionally, the ionising radiation is X-ray radiation.

There is also provided a method of irradiating at least one sample by an irradiation apparatus comprising:

outputting ionising radiation from a plurality of ionising radiation source points distributed around an irradiation volume, wherein the ionising radiation source points direct ionising radiation inwardly to the irradiation volume;

supporting the at least one sample within the irradiation volume and transporting the at least one sample along a linear path through the irradiation volume.

Optionally, there is a total of N ionising radiation source points and the method comprises selecting a number up to N of the ionising radiation source points to simultaneously activate during an irradiation cycle.

Optionally, the method comprises independently controlling operating parameters of each of the plurality of ionising radiation source points during an irradiation cycle.

Optionally, the operating parameters for an ionising radiation source point are at least one of:

an activation state (on/off) of the ionising radiation source point;

an operating current and/or an operating voltage of the ionising radiation source point;

a parameter for a beam controlling device of the ionising radiation source point.

Optionally, the method comprises acquiring image data of the irradiation volume using at least one of the radiation source points and a detector array.

Optionally, the method comprises controlling the plurality of ionising radiation source points based on the acquired image data.

An advantage of at least one example or embodiment is providing a dose of radiation above a threshold level throughout a sample (or across a plurality of samples). Properties of samples can vary. For example, a sample may have a higher density compared to other samples, or a region of a sample may have a higher density compared to other regions of the sample. Moisture content of a sample can vary the amount of radiation absorbed by the sample. The irradiation apparatus can vary a dose applied to a sample (or a region of a sample) by at least one of: energy level; irradiation time.

In a further aspect of the invention there is provided an array of ionising radiation source points comprising a ring of ionising radiation source points. This shape is advantageous as the plurality of source points may be arranged to be equidistant about a central axis of rotation of a transport apparatus.

The ring can be implemented as a ring-shaped single evacuated tube. The ring may be a continuous ring or discontinuous, having a pair of opposed ends substantially defining a ring-shaped element. The plurality of ionising radiation source points may be distributed around the ring-shaped tube. Alternatively, the plurality of ionising radiation source points can be implemented by individual sources, such as individual x-ray tubes. Other possible shapes of the array of radiation source points are a rectilinear (e.g. square) array.

Optionally, the array of ionising radiation source points comprises a plurality of rings of ionising radiation source points, wherein the rings are offset along a longitudinal axis passing through the plurality of rings.

Optionally, the array of ionising radiation source points comprises a rectilinear array.

Irradiation apparatus may be provided comprising an array of a total of N ionising radiation source points, and the irradiation apparatus may be configured to selectively simultaneously activate up to N of the ionising radiation source points during an irradiation cycle.

Optionally, the irradiation apparatus is configured to independently control operating parameters of each of the plurality of ionising radiation source points during an irradiation cycle.

Optionally, the operating parameters for an ionising radiation source point are at least one of: an activation state (i.e. on/off) of the ionising radiation source point; an operating current and/or an operating voltage of the ionising radiation source point; a parameter for a beam controlling device of the ionising radiation source point.

Optionally, the plurality of ionising radiation source points comprise at least one of: a plurality of individual ionising radiation sources; an ionising radiation source with a plurality of ionising radiation source points.

Embodiments of the invention may be understood with reference to the appended claims.

Within the scope of this application it is envisaged that the various aspects, embodiments, examples and alternatives, and in particular the individual features thereof, set out in the preceding paragraphs, in the claims and/or in the following description and drawings, may be taken independently or in any combination. For example features described in connection with one embodiment are applicable to all embodiments, unless such features are incompatible.

For the avoidance of doubt, it is to be understood that features described with respect to one aspect of the invention may be included within any other aspect of the invention, alone or in appropriate combination with one or more other features.

BRIEF DESCRIPTION OF THE DRAWINGS

One or more embodiments of the invention will now be described, by way of example only, with reference to the accompanying figures in which.

DETAILED DESCRIPTION

Figure 1:
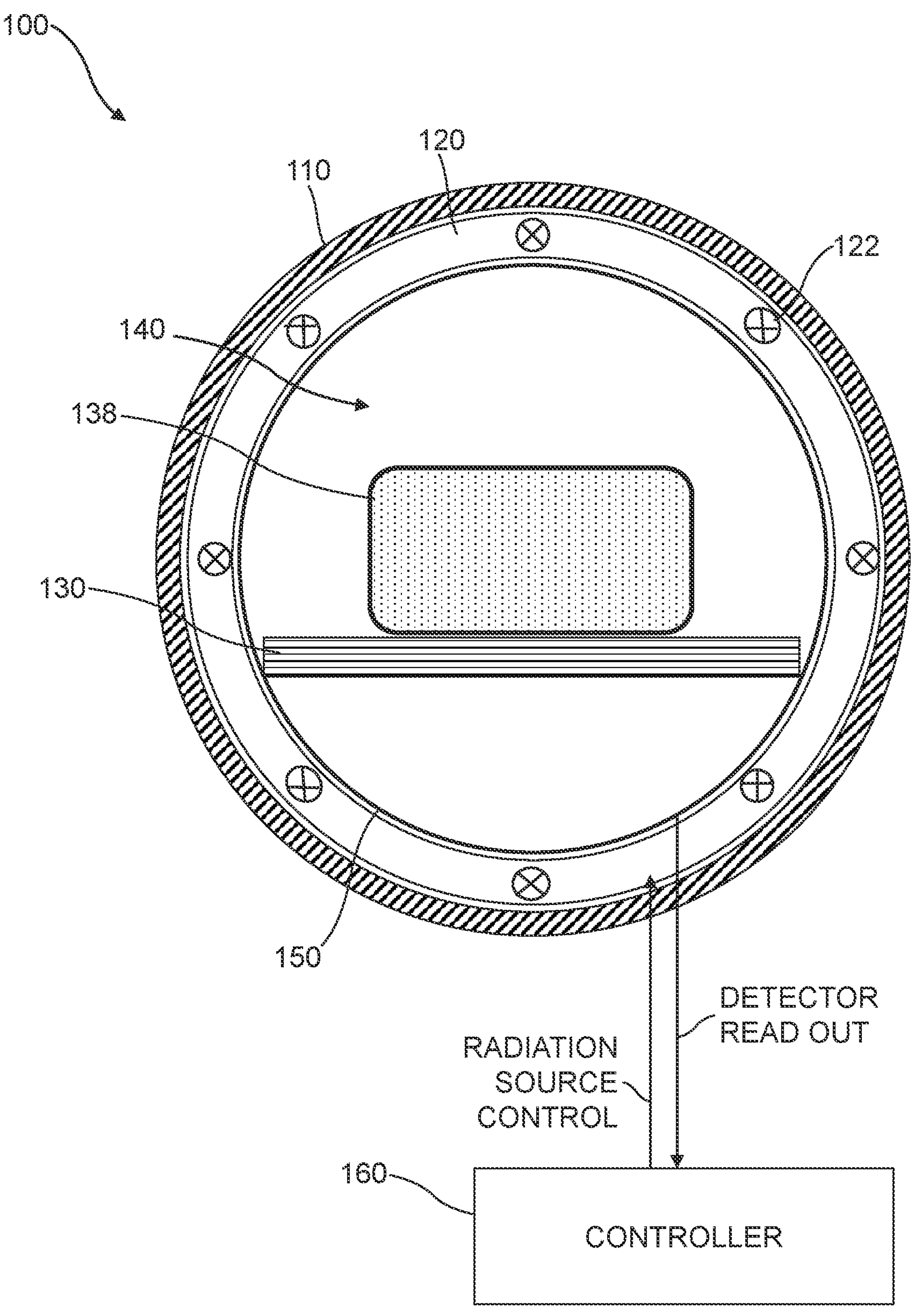
FIG. 1 shows, in cross-section, an example of an irradiation apparatus.
Figure 2:
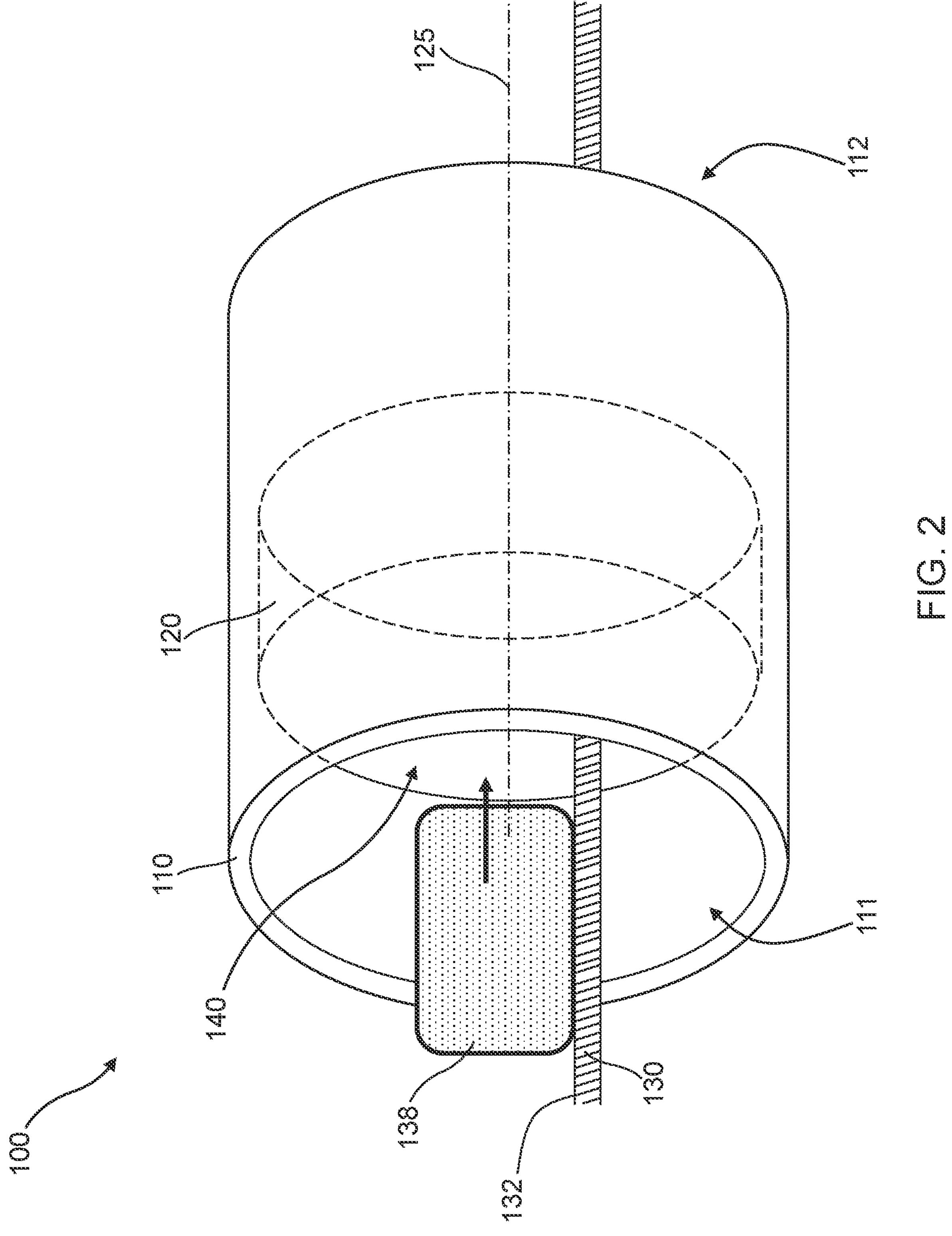
FIG. 2 shows a perspective view of an exterior of the irradiation apparatus.

FIGS. 1 and 2 shows an example of an irradiation apparatus 100. FIG. 1 shows a cross-section through the irradiation apparatus 100 and FIG. 2 shows a perspective view of an exterior of the irradiation apparatus 100. The irradiation apparatus 100 comprises a shielded housing 110. A radiation source 120, or a plurality of radiation sources; are positioned within the shielded housing 110. The shielded housing 110 prevents, or limits, passage of radiation from the radiation source 120 to an exterior of the shielded housing. In this example, the radiation source 120 has a ring shape and the shielded housing 110 is a ring of larger diameter than the radiation source 120 such that the shielded housing 110 circumferentially surrounds the radiation source 120. The shielded housing 110 has an opening at a front end 111 and at a rear end 112 to allow samples to be transported into the housing. The shielded housing 110 may extend partially across the front end 111 and/or the back end 112. In FIG. 1 the shielded housing 110 forms part of the outer housing of the apparatus 100, but it may be a separate structure which is positioned inside; or outside, of an outer housing of the apparatus 100.

The radiation source 120 can emit ionising radiation, such as X-ray radiation. X-ray radiation will be described in the following description, although it will be understood that other kinds of ionising radiation could be generated, such as gamma radiation.

The radiation source 120 has a plurality of radiation source points 122 configured to output X-ray radiation. The plurality of radiation source points 122 form an array of radiation source points 122 around an irradiation volume 140. The radiation source points 122 within the array are distributed, i.e. offset from one another. The spacing can be uniform. In FIG. 1 each of the eight radiation source points 122 is offset by 45 degrees from adjacent source points around the ring. In other examples, the spacing of the radiation source points 122 may be non-uniform. The plurality of radiation source points 122 are configured to direct X-ray radiation inwardly to the irradiation volume 140. The array of radiation source points 122 has a longitudinal axis 125.

A transport apparatus 130 is configured to support samples 138 to be irradiated. The transport apparatus 130 may be a conveyor belt or some other apparatus which can transport samples along a linear path through the irradiation volume 140. The transport apparatus 130 may comprise a planar upper surface 132, such as a belt, onto which samples 138 can be loaded. The transport apparatus 130 may comprise a plurality of holders or carriers into which samples 138 can be loaded. Each of the holders can hold a sample (e.g. an object a quantity of material) to be irradiated. For example, each holder may support a bag of blood or a quantity of loose material requiring irradiation. Samples may be placed within the holders, or may be contained within an enclosure. For example, loose material may be contained in a bag. Where holders or carriers are provided, they may be attached to the belt. Alternatively, the holders may not be attached to the belt and the holders (which have previously been loaded with a sample, or samples) may be loaded onto the belt and then removed at an output end of the irradiation apparatus. Each holder should be capable of supporting the weight of the sample requiring irradiation. Each holder can be fabricated from a material which has a low attenuation to x-rays, such as carbon fibre or aluminium. The transport apparatus 130 comprises a motor (not shown) to drive the transport apparatus.

In this example, the array of radiation source points 122 is in the form of a ring which surrounds the irradiation volume 140. Each radiation source point 122 emits radiation radially inwardly to the irradiation volume. In this example, the array of radiation source points 122 has eight radiation source points 122. The total number of radiation source points can be a smaller number or a larger number. A plane of the array of radiation source points 122 is orthogonal to the linear path of the transport apparatus 130. Advantageously, the minimum number of radiation source points is three. A large number of source points improves uniformity.

One way of implementing an X-ray source is an evacuated tube with anodes mounted at various positions along the tube. In use, a number of the anodes are selectively activated to cause radiation to be emitted from that anode. X-ray tubes are described in more detail later in this specification. Each of the radiation source points 122 can be controlled to independently emit radiation to deliver a required amount (dose) of radiation over an irradiation cycle.

Figure 3:
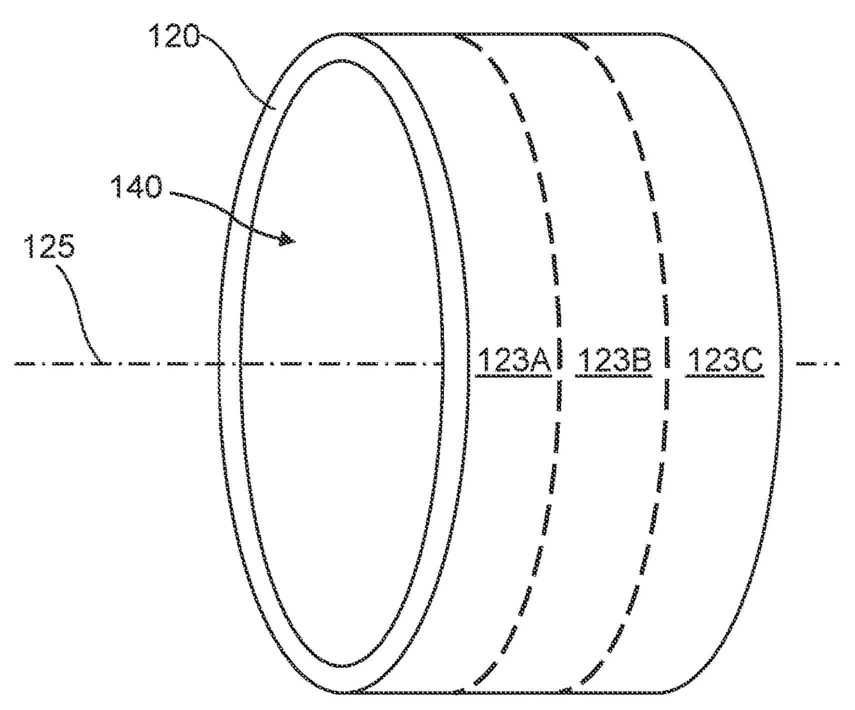
FIG. 3 shows a radiation source for use in the irradiation apparatus of FIG. 1.

A convenient shape for an evacuated tube is an annular (ring or "donut") shaped structure. FIG. 3 shows a perspective view of the radiation source 120 and irradiation volume 140. The radiation source 120 can comprise a single ring of radiation source points 122 or a plurality of rings (donuts) of radiation source points 122 which are offset along the longitudinal axis 125 of the array of radiation source points 122. A plurality of rings can be achieved by a longer evacuated tube with multiple sets of anodes, or by a plurality of evacuated tubes which are positioned along axis 125. Individual tubes may be positioned directly next to each other, or spaced apart along axis 125. FIG. 3 shows three sets of radiation source points 123A, 123B, 123C. Other numbers of sets of radiation source points can be provided. An increased number of rings improves coverage along the longitudinal axis 125.

The irradiation apparatus 100 may also comprise a detector array 150 which can be used for imaging the irradiation volume 140. The term "Imaging" means obtaining information about properties of samples within the irradiation volume 140. It is useful to know properties such as density of samples. The detector array 150 comprises a plurality of detectors which are capable of detecting X-ray radiation (or other radiation used by the radiation source points 122). The detector array 150 is shown as a circular array with a central axis aligned with the axis 125. The detector array 150 may extend around all, or only part, of the transport apparatus 130. For example, a detector array 150 may be provided in a region opposite one of the radiation source points 122. The detector array 150 comprises a grid of detector elements or devices which provide pixels of an image. An output of the detector array 150 is connected to read out circuitry.

The irradiation apparatus 100 comprises a controller 160. The controller 160 controls operation of the radiation source 120, such as switching radiation source points 122 on and off, and controlling an output level of the radiation source 120. The controller 160 controls operation of the detector array 150. The controller 160 may be positioned in the same unit 100 as other parts of the apparatus, or separately from the main unit. It will be understood the radiation source 120 comprises other elements not shown in these FIGURES, such as a power supply.

Figure 4:
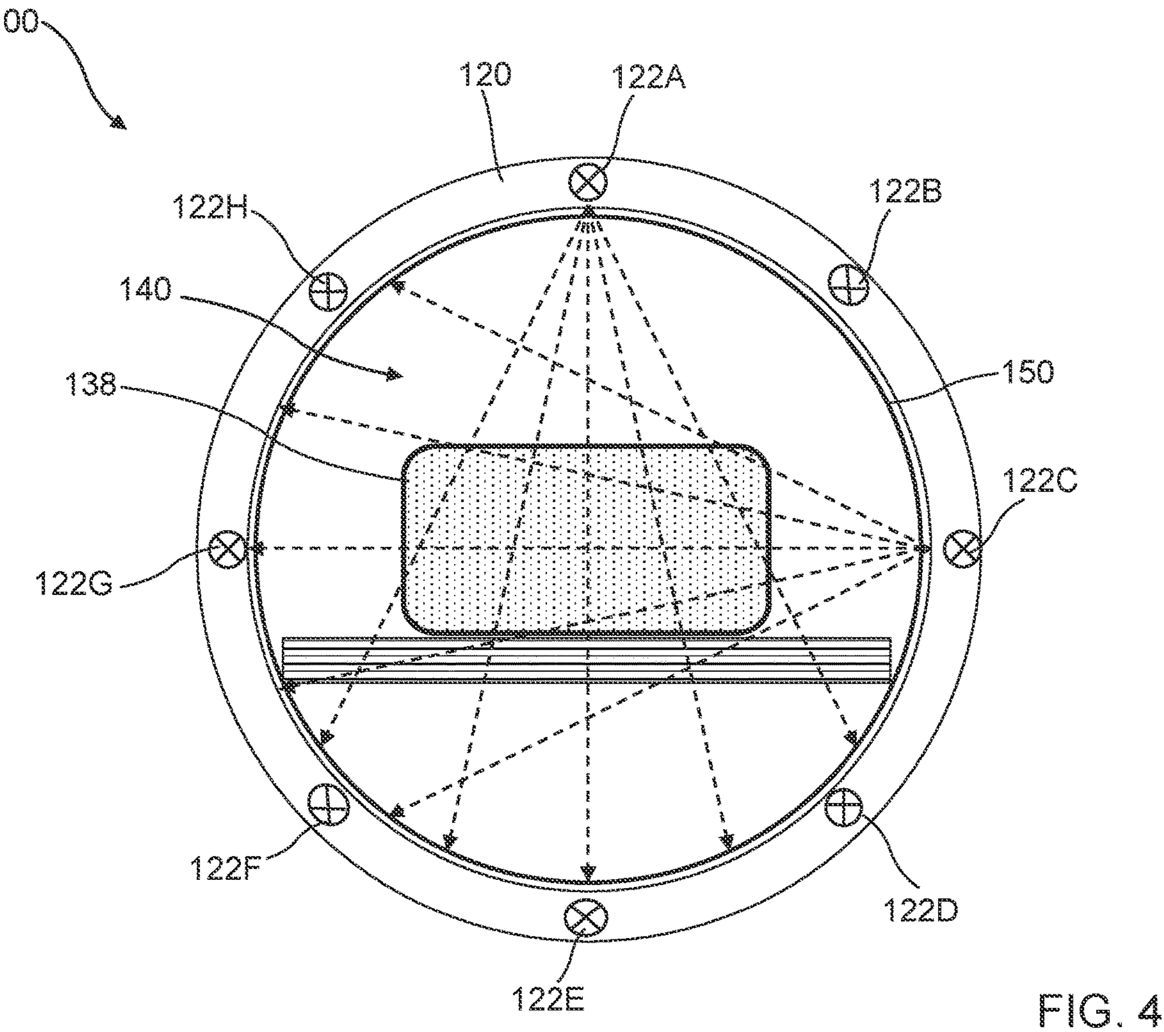
FIG. 4 shows the irradiation apparatus in use.

FIG. 4 shows the radiation source 120 and the irradiation volume 140 of FIG. 1 in use. In this example, the radiation source 120 has eight radiation source points: 122A-122H. For clarity, only two of these radiation source points 122A, 1220 are shown emitting radiation. The irradiation apparatus 100 can simultaneously activate between one and eight of the radiation source points 122A-122H. It can be seen that emitting radiation from a variety of different directions around the irradiation volume 140 can achieve a more uniform dose of samples.

Figure 5:
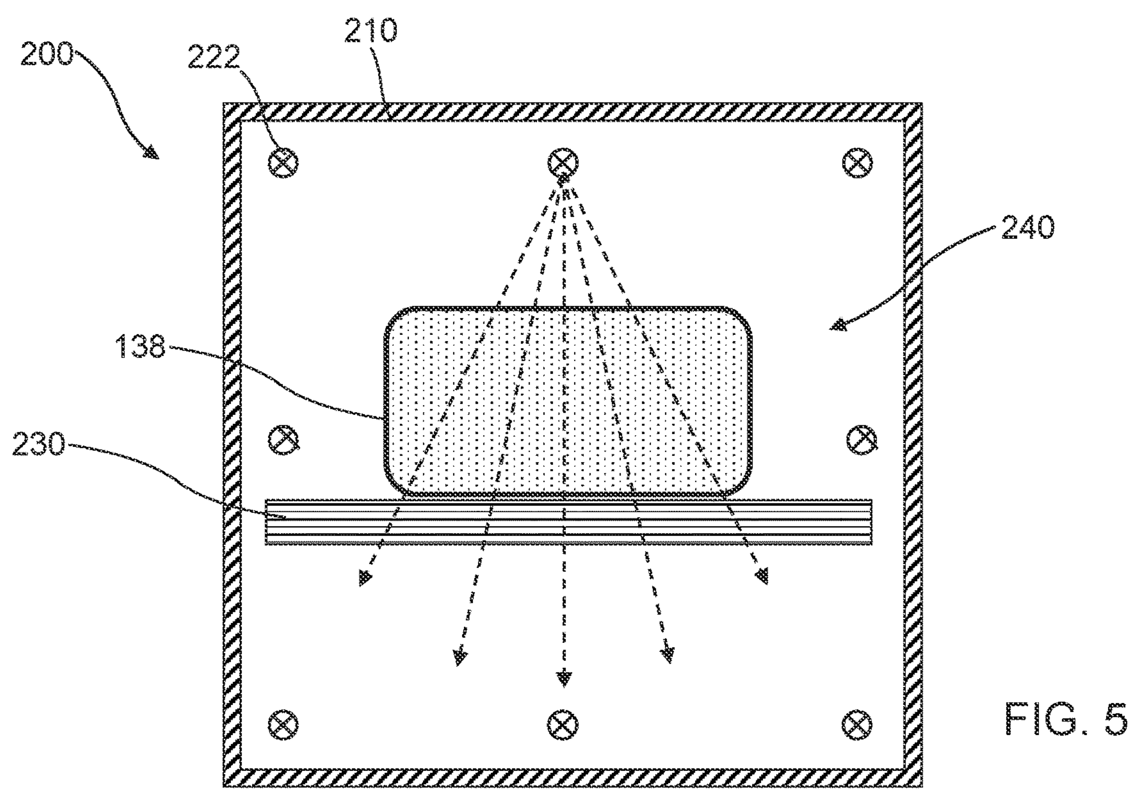
FIG. 5 shows an example of imaging samples using an irradiation apparatus.

Another way of implementing the radiation source points 122 is by discrete (i.e. individual) radiation sources. FIG. 5 shows a cross sectional view of another example of an irradiation apparatus 200. The irradiation apparatus 100 comprises a shielded housing 210, a transport apparatus 230 and an irradiation volume 240 as described above. In this example, the radiation source 220 comprises a plurality of radiation source points 222 which are implemented by a plurality of individual sources. The radiation sources can be mounted to an interior face of the shielded housing 210, supported by a structure within the shielded housing, or some other way. The radiation sources 222 can be positioned in a differently shaped array. In this example, the radiation sources 222 are arranged in a rectilinear array.

The irradiation apparatus 100, 200 may also be capable of performing imaging of the irradiation volume. That is, the irradiation apparatus acquires data about samples within the irradiation volume. This can be useful to determine properties of the materials requiring irradiation (e.g. density) and the optimum use of the radiation sources (e.g. number of sources, output power, beam width), It can also detect foreign objects within the irradiation volume 140.

X-rays travel in straight lines, emerging as a beam from one of the radiation source points 122. X-rays will either travel through materials with a varying degree of attenuation (e.g. non-metal materials) or will be scattered or absorbed by certain materials, such as metal. The amount of radiation that is received at a detector is indicative of the properties of the sample, such as: material type; density.

Figure 6:
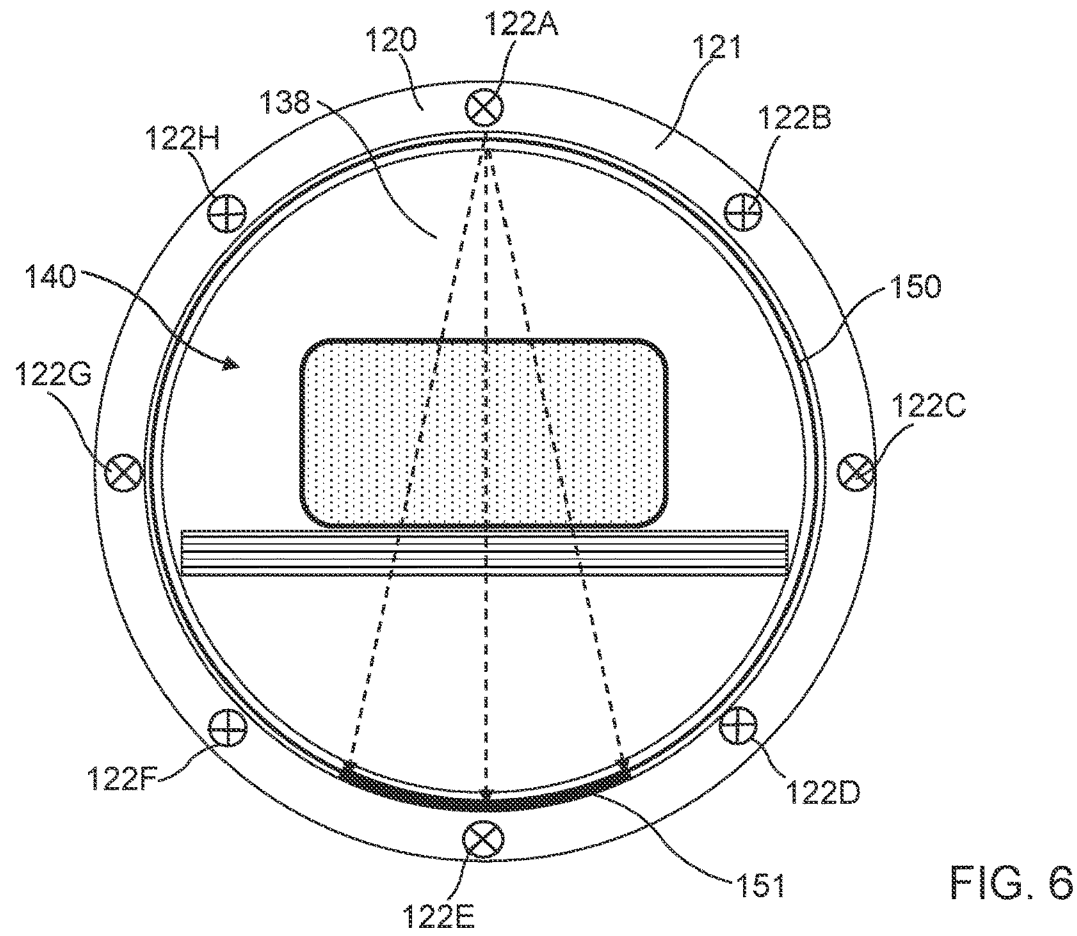
FIG. 6 shows an example of an irradiation apparatus with individual radiation sources.

FIG. 6 shows an example of an irradiation apparatus configured for imaging samples. A radiation source point 122 and a region of the detector array opposite to the radiation source point are used as a pair for imaging purposes. In the example shown in FIG. 6, radiation source point 122A is activated to emit radiation for imaging, and a region 151 (shown in bold) of the detector array 150 is used to detect radiation received from source point 122A. Region 151 may be a portion of the overall detector array 150. In a simplified apparatus with a smaller detector array, region 151 may be the entire detector array.

More than one source-detector pair may be activated at the same time. For example, a first source-detector pair and a second source-detector pair may be activated simultaneously. Advantageously, the first source-detector pair and the second source-detector pair are orthogonal to one another. In FIG. 6, radiation source points 122A and 1220 are orthogonal to one another.

The one or more of the radiation source points are operated at a relatively low power level for imaging purposes. The radiation levels used for imaging are significantly lower than the radiation levels used for irradiation.

There are various ways of acquiring image data for samples 138 within the irradiation volume. One way of acquiring image data is to use one of the source-detector pairs, or a sequence of source-detector pairs, while the transport apparatus 130 is controlled to remain stationary. An example sequence can be as follows:

(i) activate radiation source point 122A and detect radiation at a position opposite to radiation source point 122A;

(ii) activate radiation source point 122B and detect radiation at a position opposite to radiation source point 122B;

and continuing in the same manner around the plurality of radiation source points 1220-122H.

Using a plurality of source-detector pairs can allow imaging of a larger sample. It is possible to determine a three-dimensional image from a set of image data of a sample acquired from different directions. This is called computed tomography (CT). CT is known and will not be described further.

In an example where multiple radiation-source points are simultaneously used, the sequence can be as follows:

(i) activate radiation source point 122A and detect radiation at a position opposite to radiation source point 122A and activate radiation source point 1220 and detect radiation at a position opposite to radiation source point 1220;

(ii) activate radiation source point 122B and detect radiation at a position opposite to radiation source point 122B and activate radiation source point 122D and detect radiation at a position opposite to radiation source point 122D;

(iii) activate radiation source point 122E and detect radiation at a position opposite to radiation source point 122E and activate radiation source point 122G and detect radiation at a position opposite to radiation source point 122G;

(iv) activate radiation source point 122F and detect radiation at a position opposite to radiation source point 122F and activate radiation source point 122H and detect radiation at a position opposite to radiation source point 122H.

Referring again to FIG. 2, samples 138 carried by the transport apparatus 130 extend in a direction which is parallel to the axis 125, i.e. an axial direction. It is desirable to image the entire volume of samples. This can be achieved in various ways. One possible way of imaging samples 138 along the axial dimension is to perform a sequence of imaging operations for different relative positions between the detector array 150 and the sample 138 carried by the transport apparatus 130. This can allow for a detector array 150 with a fairly short axial dimension. For each relative position of the detector array 150 and the sample 138, the detector array 150 acquires an image of part (i.e. a slice) of sample 138. The transport apparatus 130 can be configured to move the sample 138 at an axial speed which allows a required image quality. Imaging data can be repeatedly (or continuously) acquired from one source-detector pair, or by repeatedly activating a plurality of different source-detector pairs. Alternatively, the transport apparatus 130 can be configured to repeatedly: (i) move the sample 138 forward and then (ii) cause the sample 138 to be stationary while imaging data is acquired. For each axial position the imaging data can be acquired for one source-detector pair, or a plurality of different source-detector pairs.

Another possible way of imaging samples 138 along the axial dimension is to provide a detector array 150 which extends for an axial distance which is at least as long as the samples. The transport apparatus 130 can be configured to move the sample 138 into the detector array 150 then cause the sample 138 to be stationary while imaging data is acquired. The imaging data can be acquired for one source-detector pair, or a plurality of different source-detector pairs.

Figure 7:
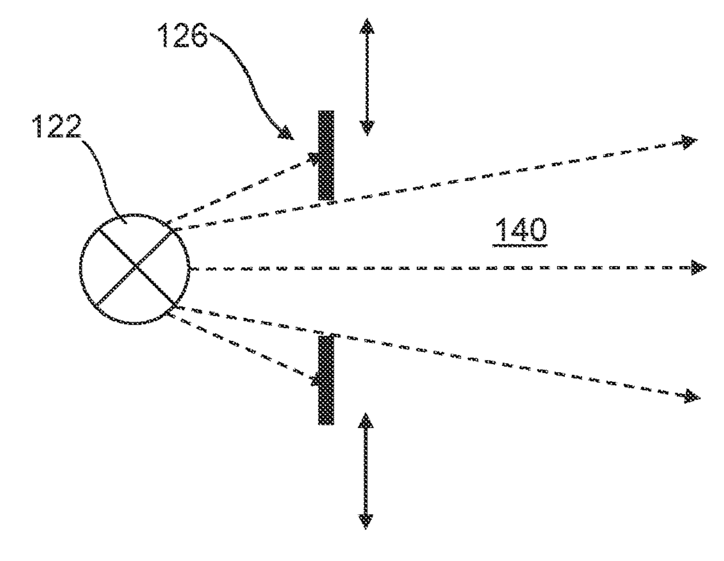
FIG. 7 shows a radiation source point and a beam controlling device.

FIG. 7 shows a radiation source point 122 and a beam controlling device or collimator 126. The beam controlling device 126 can be controlled to vary a size of an opening or aperture. This controls shape and/or width of a beam of radiation emitted by the radiation source point 122 towards the irradiation volume 140. A beam controlling device 126 can be provided for each radiation source point 122, 222.

It is to be understood that the ability to acquire images of a sample from different directions, such as by the method described above, enables information in respect of a variation in density of a sample within the sample to be obtained. It also provides information in respect of a volumetric and spatial distribution of the sample to be determined. The relative location of the sample holder 134 and/or packaging of a sample of interest may also be determined.

This increased understanding of density with volumetric and spatial distribution information made available by embodiments of the present invention may be advantageous for certain applications.

Firstly, X-ray radiation having an energy below around 300 KV has been shown to be more effective in microbial remediation than higher energy sources (such as gamma radiation and high energy X-ray radiation), However, at these lower energies, the X-ray absorption and scatter by samples is much greater and therefore the radiation does not penetrate through as much of the sample in as uniform a way as with high energy gamma and X-ray sources. The increased absorption and scatter of these lower energy X-rays will cause the dose delivered to the samples and sample packaging at different densities, volumes and spatial distributions to vary much more significantly than higher energy gamma and X-ray sources. Care in planning the dose delivery to the sample is therefore much more important and the described imaging steps can enable a plan for uniform low energy X-ray dose delivery to all parts of the sample to be created relatively quickly.

Secondly, the imaging step may allow optimization of power (energy saving) and throughput by ensuring that the required dose is reached for all parts of the sample with limited amounts of the sample receiving more dose than is required. This may also be described as an improved Dose Uniformity Ratio.

Thirdly, many types of produce such as meats, fruits, spices and vegetative crops such as *cannabis* can have multiple types of packaging material surrounding the sample to be irradiated and these packaging changes must be considered when determining dose levels to be applied to the samples. Thus, the amount of absorption of X-ray radiation by the packaging may be taken into account in some embodiments, and the dose of X-ray radiation to which the item (sample and packaging) is subject may be adjusted accordingly in order to ensure that the required dose to the sample, within the packaging, is achieved. The amount of absorption of X-ray radiation by a sample holder such as a holder 134 associated with the apparatus 100 may be taken into account in some embodiments, and the dose of X-ray radiation to which the holder 134 and sample 138 is subject may be adjusted accordingly in order to ensure that the required dose to the sample 138, within the holder 134, is achieved.

Fourthly, X-ray irradiation of the samples in the desired end product packaging has the advantage that downstream handling of the samples is made easier since a reduction in the risk of recontamination of the sample during downstream handling may be achieved.

Fifthly, customers looking to use X-ray irradiation apparatus according to embodiments of the present invention for sterilization may wish to irradiate samples that vary greatly in density, as well as in volume and spatial distribution of the sample in the irradiation field, but which also vary greatly in the density and spatial distribution of the different packaging types that they use with samples. The determination of the dose provided by different irradiation sources around the sample based on the 3D image of the sample and associated sample packaging allows the user to compensate for both variations in sample density and spatial distribution as well as the nature of the sample packaging such as packaging material composition and thickness. The user may therefore use the apparatus to irradiate a range of different sample types and different sample packaging materials whilst still providing the desired dose to substantially the entire sample based on the analysis of the imaging results.

It is to be understood that, in some embodiments as described herein, the imaging step can utilize the same irradiation sources as the irradiation step allowing for more simple and lower cost apparatus. Furthermore, the imaging and irradiation functions may be performed by the same apparatus, leading to improved workflow and throughput.

As noted above, it is to be understood that the presence of a sample holder in the path of a beam through the sample to be irradiated may also be taken into account when considering the amount of radiation that a sample itself will receive.

It is to be understood that packaging of the sample may create areas of higher density and lower density of materials surrounding the samples 138 to be irradiated, and these areas can be detected by X-ray imaging. For example, a sample may be packaged in multiple sealed containers that are held in a rack with the containers side by side or stacked on top of each other or both. The beams that are used to irradiate the sample will encounter different densities of materials in the packaging and in the sample contained in the packaging based on the density and number of containers that each beam being projected from each irradiation source encounters as it passes through the rack. Each beam will also encounter different densities of materials due to the different packaging materials used in each container such as plastics or metal covers on the top of the container versus materials such as plastics, glass, cardboard or other materials used in the rest of the container.

Apparatus according to embodiments of the present invention is able to determine a required amount of irradiation to which the irradiation volume is to be subject in order to deliver the required dose of radiation to the sample(s) 138. In some embodiments the apparatus is able to determine the amount of radiation to which the irradiation volume is to be subject as the sample 138 is moved in the irradiation volume 138 in order to deliver the required dose to different regions of the sample 138. The apparatus controls the respective X-ray radiation sources accordingly in order to deliver the required dose to the different regions. For example, denser regions of the sample may receive more radiation. In some embodiments, regions of a sample with a higher moisture content may receive a higher dose than regions with a lower moisture content in order to compensate for absorption of radiation by the moisture. Similarly, where radiation is directed to pass through one or more sample holders such as one or more containers and optionally one or more racks or other structural elements within the irradiation volume, the apparatus may take such items into account in determining the required amount of radiation to be delivered by a given radiation source at a given moment in time as the sample is moved.

In some embodiments the sample may be moved intermittently or at a speed that varies as a function of time in order to ensure that the required dose is delivered.

In addition, it is expected that in some cases a user may wish to irradiate the sample inside the final packaging in a sealed state so the sample inside the container, after the irradiation process is completed, can be considered fully decontaminated within the final packaging and no further manipulation of the sample and potential re-contamination can occur prior to the sample being delivered or purchased by the consumer.

In some embodiments, in addition to or instead of the apparatus determining an amount of X-ray radiation to which an irradiation volume is to be exposed, compensating for X-ray absorption due to packaging and/or sample holder (s), based on acquired image data, the apparatus may determine the amount of radiation to be applied to the irradiation volume at least in part based on data input by a user. For example, the user may be able to input data such as data indicative of the type of packaging material being used (e.g. indicative of material and thickness) and/or the presence of one or more sample holders or other items such as portions of the apparatus 100 in the irradiation volume. The apparatus 100 may apply a correction to the amount of X-ray radiation applied to the irradiation volume based at least in part on the data input by the user and stored data, such as data indicative of the amount of radiation absorbed by a given type of packaging and/or sample holder. Thus, the apparatus 100 may compensate for an amount of radiation applied to the irradiation volume that would not irradiate the sample due to absorption or scattering by sample packaging and/or sample holder(s) or other items in the irradiation volume, by increasing the amount of radiation applied in a corresponding manner.

Figure 8:
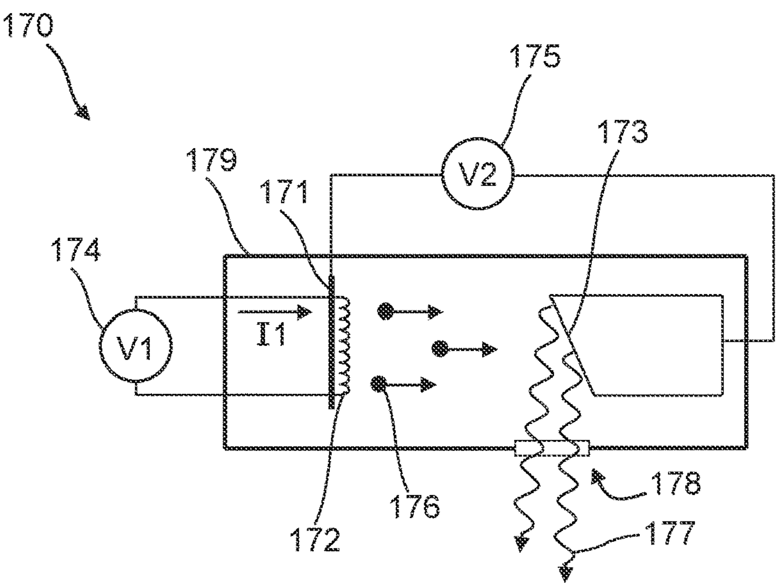
FIG. 8 shows an example of a reflection type of x-ray tube.
Figure 9:
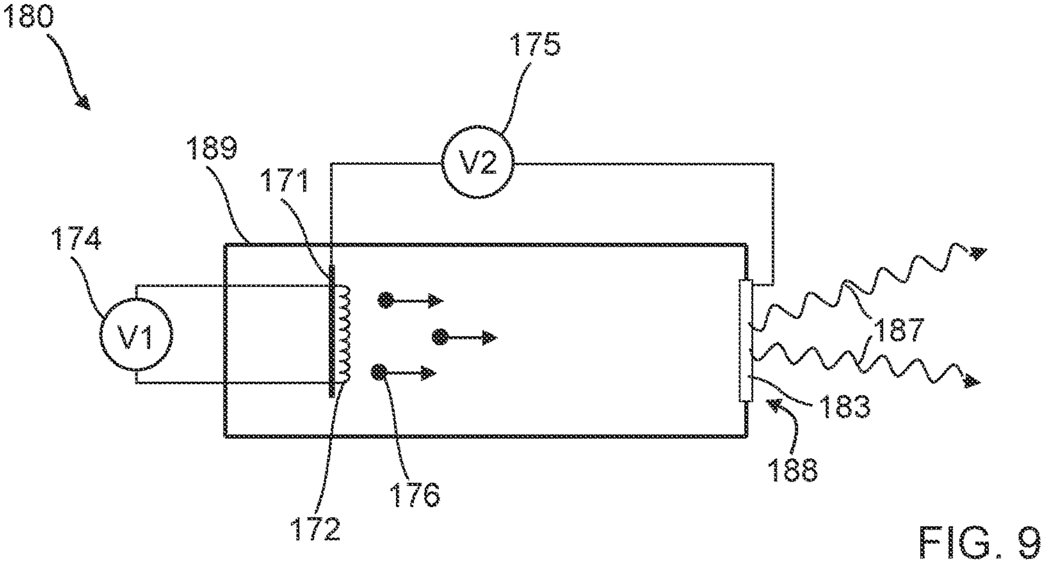
FIG. 9 shows an example of a transmission type of x-ray tube.

FIGS. 8 and 9 show examples of two types of x-ray tube 170, 180 which can be used to provide one of the x-ray source points 122, 222 shown in FIGS. 1, 4, 5 and 6.

FIG. 8 shows an example x-ray tube 170 which emits x-rays 177 through a side window 178. This window 178 can form one of the x-ray source points 122, 222 shown in FIGS. 1, 4, 5 and 6. This type of x-ray tube 170 is called a Coolidge type x-ray tube or a reflection type x-ray tube. The x-ray tube 170 has a cathode 171, a filament 172 and an anode 173. A power supply 174 is connected to the filament 172. The filament 172 is typically made of metal with a high melting point. The power supply 174 is configured to supply a voltage V1 across the filament 172, An electrical current I1 flows through the filament 172. This is called the tube current. The current flow heats the filament and causes the filament to emit electrons 176 by thermionic emission. A power supply 175 is connected to the cathode 171 and to the anode 173. The power supply 175 is configured to supply a voltage V2 between the anode 173 and the cathode 171, Power supply 175 is a high voltage power supply, typically of more than 20 kV. In use, electrons 176 are accelerated towards the anode 173 due to the high voltage V2, Collision of electrons with the anode 173 causes emission of Bremsstrahlung radiation. The Bremsstrahlung radiation has a broad spectrum and includes heat and x-ray photons (x-rays) 177. A filter may be provided at the window 178 to absorb low energy photons.

FIG. 9 shows an example x-ray tube 180 which emits x-rays 187 through an end window 188. This window 188 can form one of the x-ray source points 122, 222 shown in FIGS. 1, 4, 5 and 6. This type of x-ray tube 180 is called a transmission source. Many of the features are the same as FIG. 8 and are labelled with the same reference numerals. Operation of this tube is similar to FIG. 8 and only the main differences will be described. The x-ray tube 180 has a cathode 171, a filament 172 and an anode 183. The anode 183 forms an end window in housing 189 of the x-ray tube, or the anode 183 can be positioned adjacent to an end window of the housing of the x-ray tube. A filter may be provided at the window 188 to absorb low energy photons. One advantage of this type of x-ray tube is improved heat dissipation as the anode 183 is now part of, or nearer to, the external surface of the housing and is not contained within the housing 189.

The x-ray tubes 170, 180 comprise a housing or chamber 179, 189 which is typically formed of metal or glass. The housing 179, 189 is evacuated, i.e. the interior of the housing is a vacuum. The housing 179, 189 is shielded, apart from at the window 178, 188. The shielding reduces, or prevents, unwanted emission of radiation. In FIG. 8 the window 178 is provided on a side of the housing 179, alongside the anode 173. In FIG. 9 the window 188 is provided at an end of the housing 189, and x-rays are emitted from the anode 183 through the end window.

Figure 10:
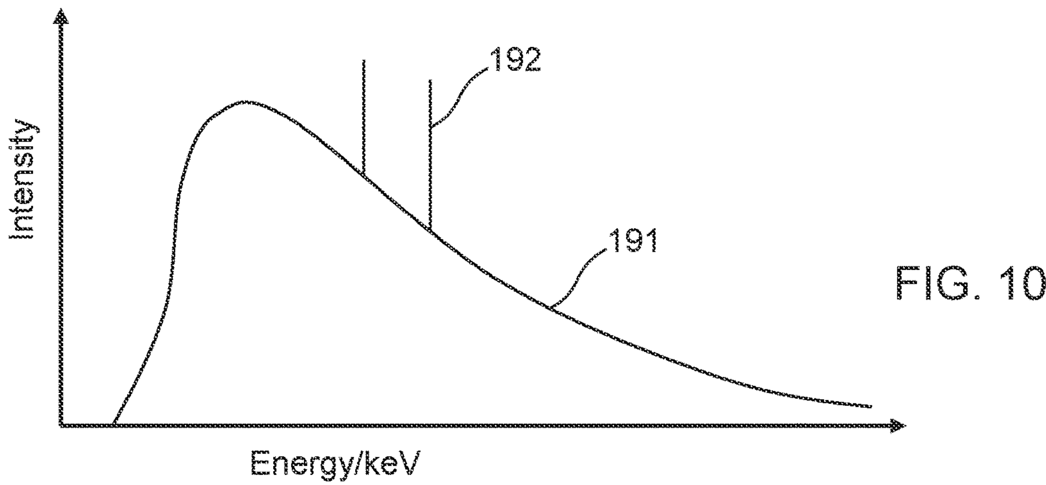
FIG. 10 shows an example graph of x-ray emissions from an x-ray tube.

FIG. 10 shows a graph of Bremsstrahlung radiation output by the x-ray tubes 170, 180. The vertical axis represents intensity, or number of photons. The horizontal axis represents energy per photon. The graph has a general curved shape 191, and may include one or more peaks 192 at particular energy values. Energy at low values may be removed by the filter at the window. Increasing the voltage V2 between the anode 173, 183 and the cathode 171 increases the energy of electrons 176 striking the anode 173, 183 and increases number of higher-energy x-ray photons. This has the effect of widening the graph of FIG. 10. Increasing the voltage V1 across the filament 172 (i.e. the tube current I1) increases the rate of thermionic emission and the flow of electrons towards the anode and increases the number of x-ray photons generated at the anode. This increases the intensity (y-axis), but the overall shape of the graph remains the same.

The total dose of x-ray radiation delivered to a sample depends on: x-ray tube current (I1) which controls a number of x-ray photons emitted; x-ray tube voltage (V2) which controls energy of emitted x-ray photons; and time for which radiation is emitted, i.e. the irradiation cycle.

Figure 11A:
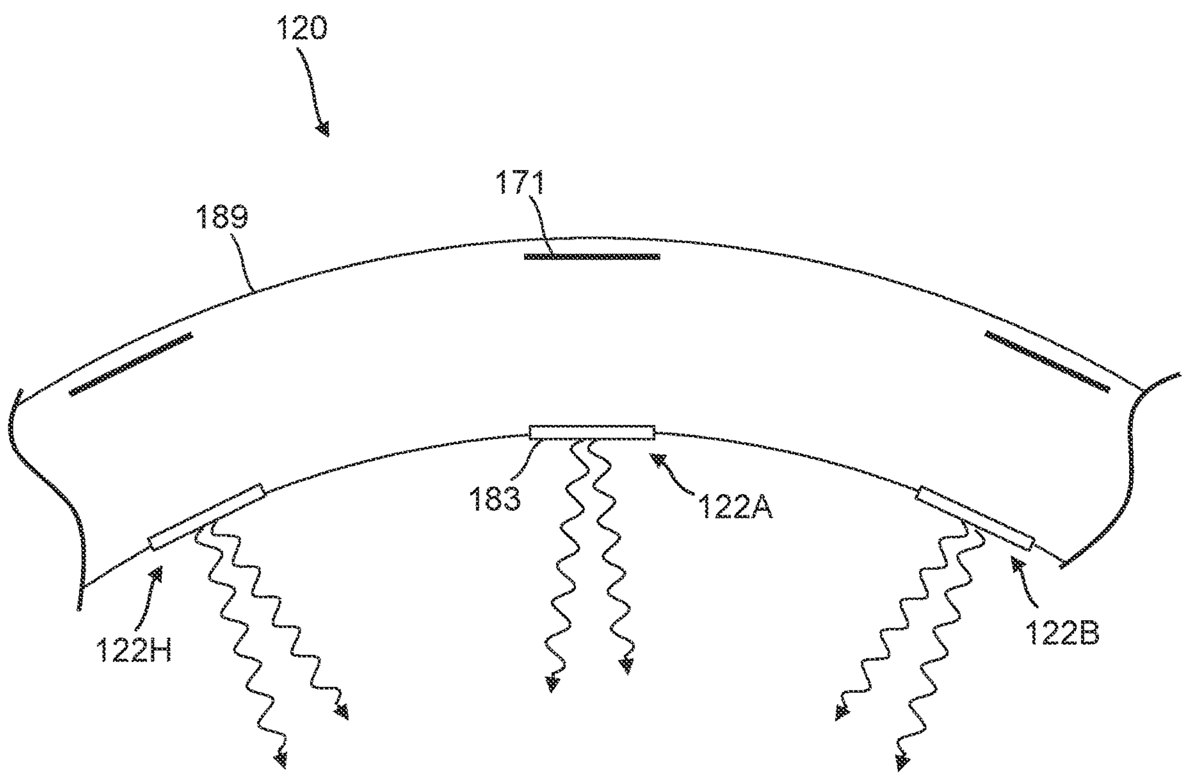
FIG. 11 shows (a) part of an example of a ring-shaped x-ray radiation source, (b) the whole of the ring-shaped source shown in (a), and (c) an alternative design in which the tube has a discontinuity, a gap being provided between opposed proximate ends of the tube.
Figure 11:
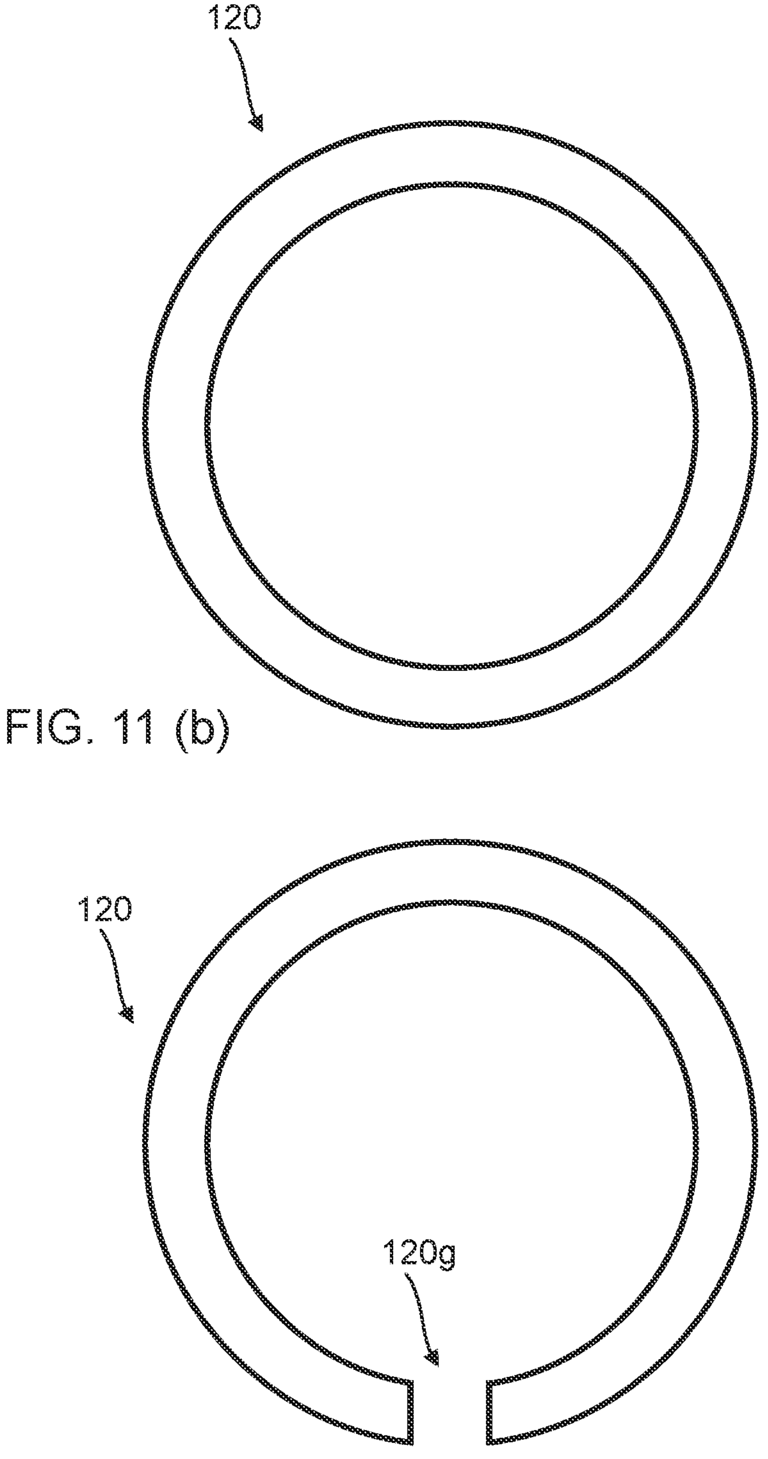

The irradiation apparatus can comprise a single ring-shaped x-ray tube 120 with a plurality of radiation source points 122 (FIG. 1, 4, 6), or a plurality of x-ray tubes with each x-ray tube having an x-ray source point 222 (FIG. 5). For the case of a plurality of x-ray tubes, each x-ray tube can be of the type shown in FIG. 8 or 9. The x-ray tubes can be positioned at required positions within the shielded housing to form the array of radiation source points. For the case of a single ring-shaped x-ray tube 120, there is a single ring-shaped evacuated housing 189. FIG. 11(*a*) shows part of an example of a ring-shaped x-ray source 120. The features shown in FIG. 8 or 9 (i.e. anode, filament, cathode and window) are replicated at positions around the housing. For example, the x-ray source 120 of FIG. 4 with eight source points 122A-122H can have a single ring-shaped housing 189 with eight instances of the apparatus shown in FIG. 8 or 9 at eight positions around the housing 189.

In a further alternative, the ring-shaped x-ray source 120 can have a single continuous ring-shaped anode. The anode can be held at a high positive potential and cathodes can be individually, or collectively, turned on by control of a potential applied to each cathode.

A power supply can provide a voltage V1/current to each instance of the apparatus to control intensity of x-ray radiation emitted from the respective x-ray source point. A power supply can provide a voltage V2 to each instance of the apparatus to control energy of x-ray radiation emitted from the respective x-ray source point. Each power supply can independently control the voltage(s) applied to each instance of the apparatus.

It will be understood that a single power supply can be provided to generate V1 and V2, or a separate power supply can be provided to generate each of V1 and V2. A power supply may generate V1 and/or V2 for all of the radiation source points 122. Alternatively, a separate power supply may be provided for each of the radiation source points 122.

The power supply, or power supplies, can independently control the voltage(s) applied to the cathodes, anodes and filaments to independently control x-ray radiation output by each radiation source point 122.

FIG. 11(*b*) shows the full single ring-shaped x-ray tube 120 a portion of which is shown in FIG. 11(*a*). FIG. 11(*c*) shows an alternative design for the single ring-shaped x-ray tube 120 in which the tube 120 has a discontinuity, a gap 120*g* being provided between opposed proximate ends of the tube 120. Such a design may be easier to fabricate and/or provide for more convenient maintenance.

Figure 12:
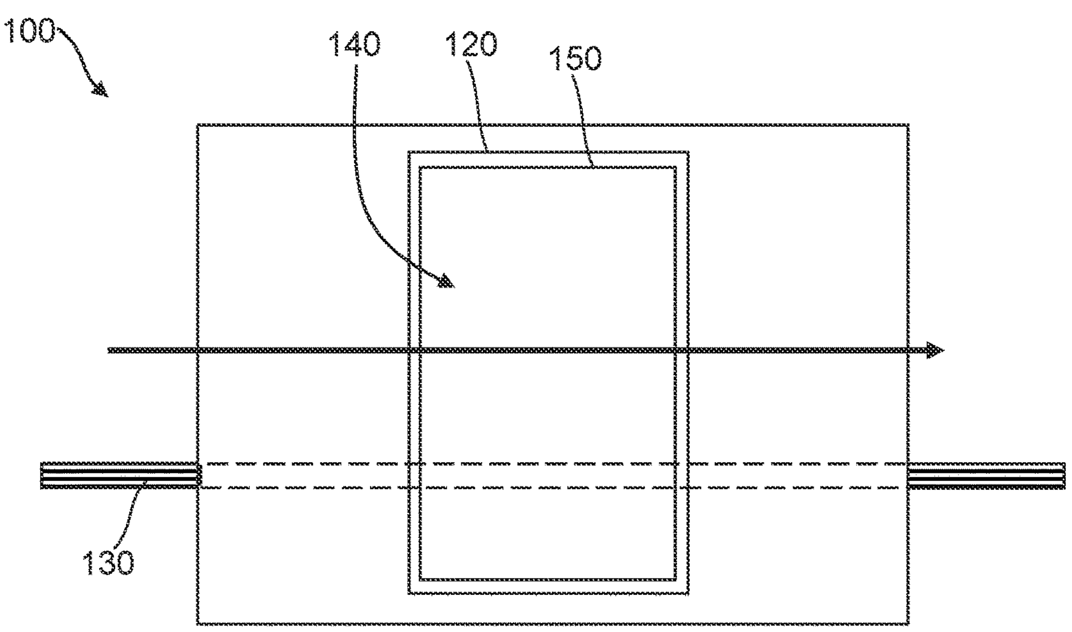
FIG. 12 shows an irradiation apparatus with an array of radiation source points used for imaging and irradiation.

The irradiation apparatus 100 may comprise a radiation source 120 and a detector array 150 which are co-located. This is shown in FIG. 12. In use, the irradiation apparatus 100 may firstly use the radiation source 120 and the detector array 150 to acquire imaging data about one or more samples. The radiation source 120 can be controlled to operate at a low radiation level. Then, the irradiation apparatus 100 may use the same radiation source 120 to irradiate the one or more samples at a higher radiation level. The transport apparatus 130 may be controlled to move the samples into, or through, the irradiation volume 140 while the imaging is performed. Then, the transport apparatus 130 may be controlled to move the samples into, or through, the irradiation volume 140 while the irradiation is performed. Depending on the length of the irradiation volume 140 relative to the samples, the transport apparatus 130 may be controlled to slowly pass the sample through the irradiation volume 140 in a scanning operation, or to hold the sample within the irradiation volume 140. For samples which are longer than the irradiation volume, a scanning operation is advantageous. The transport apparatus 130 may be controlled to: (i) transport a sample into the irradiation volume for imaging; (ii) transport the sample out of the irradiation volume; and (iii) transport the sample into the irradiation volume for irradiation.

Figure 13:
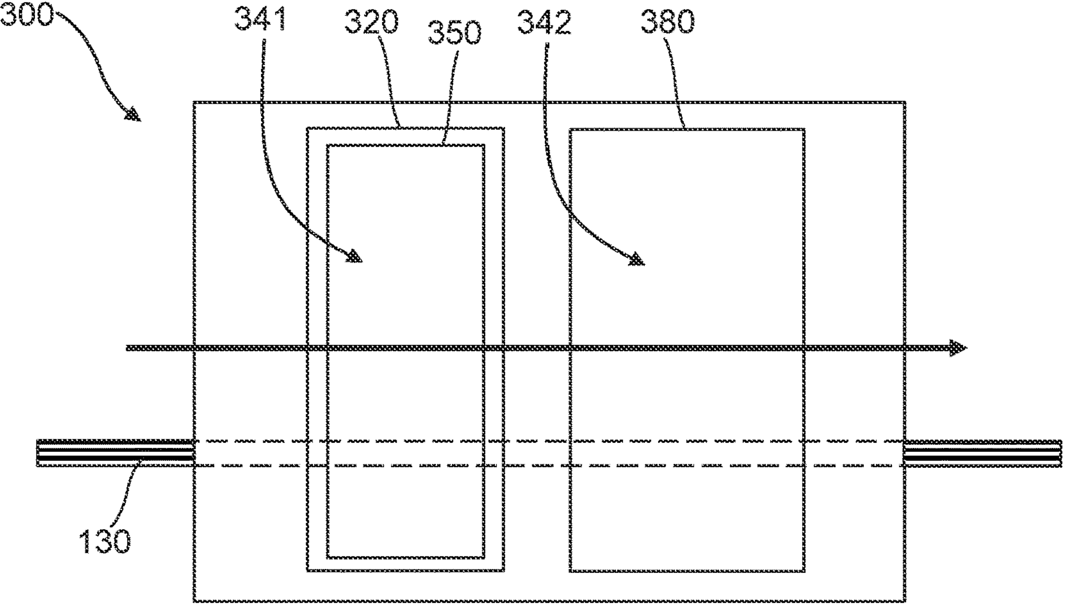
FIG. 13 shows an irradiation apparatus with a first array of radiation source points used for imaging and a second array of radiation source points used for irradiation.

FIG. 13 shows another example of irradiation apparatus 300 which comprises a first radiation source 320 and a detector array 350 which are co-located for imaging purposes. The first radiation source 320 may be the same, or similar to the radiation source 120. The detector array 350 may be the same, or similar, to the detector array 150. The irradiation apparatus 300 also comprises a second radiation source 380 for irradiation purposes. The second radiation source 380 may be the same, or similar to the radiation source 120. In use, the irradiation apparatus 300 may firstly use the radiation source 320 and the detector array 350 to acquire imaging data about one or more samples. The radiation source 320 can be controlled to operate at a low radiation level. Then, the irradiation apparatus 300 may use the radiation source 380 to irradiate the one or more samples at a higher radiation level. The transport apparatus 130 is controlled to move the samples into the volume 341 (imaging volume) within the radiation source 320 and the detector array 350 and then hold the samples within the imaging volume 341, or move the samples at a slow rate through the imaging volume 341, while the imaging is performed. Then, the transport apparatus 130 is controlled to move the samples from the imaging volume 341 to the irradiation volume 342 within the radiation source 380. During irradiation the transport apparatus 130 is controlled to hold the samples within the irradiation volume 342, or move the samples at a slow rate through the irradiation volume 342. After irradiation, the transport apparatus 130 is controlled to move the samples out of the irradiation volume 342. Similar to FIG. 7, the transport apparatus 130 may be controlled to slowly pass the sample through the imaging volume 341 and/or the irradiation volume 342 in a scanning operation, or to hold the sample within the imaging volume 341 and/or the irradiation volume 342. For samples which are longer than the imaging/irradiation volumes, a scanning operation is advantageous.

Figure 14A:
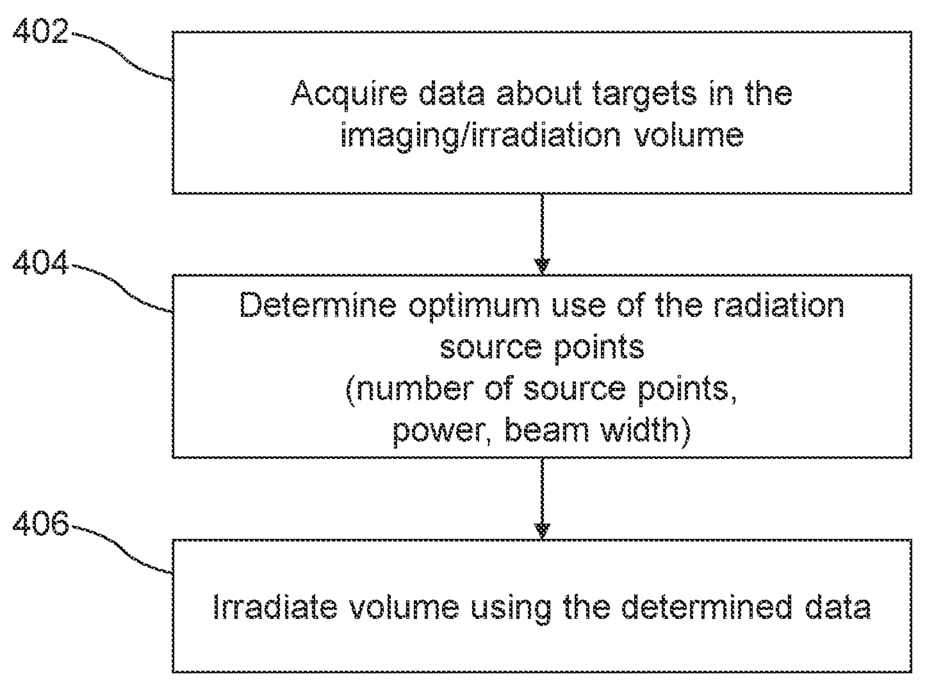
FIG. 14(*a*) shows a method of operating the irradiation apparatus, FIG. 14(*b*) illustrates schematically an acquired image of a sample inside packaging and FIG. 14(*c*) illustrates a further method of operating the irradiation apparatus.
Figure 14B:
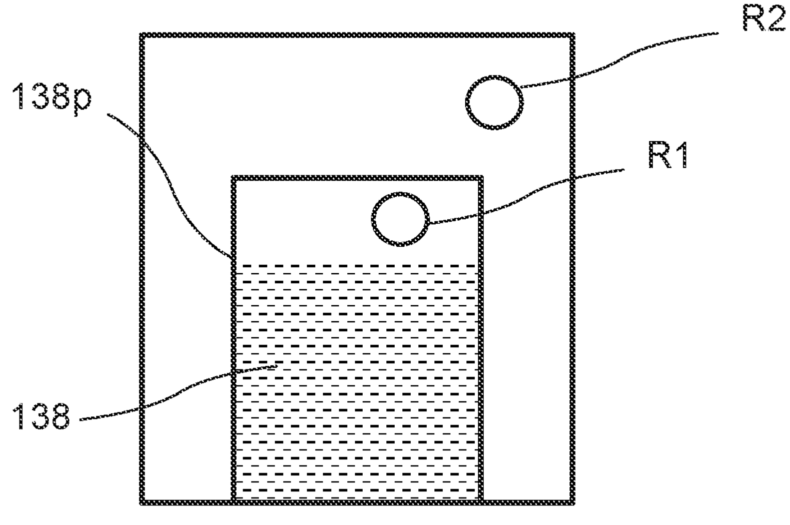
Figure 14C:
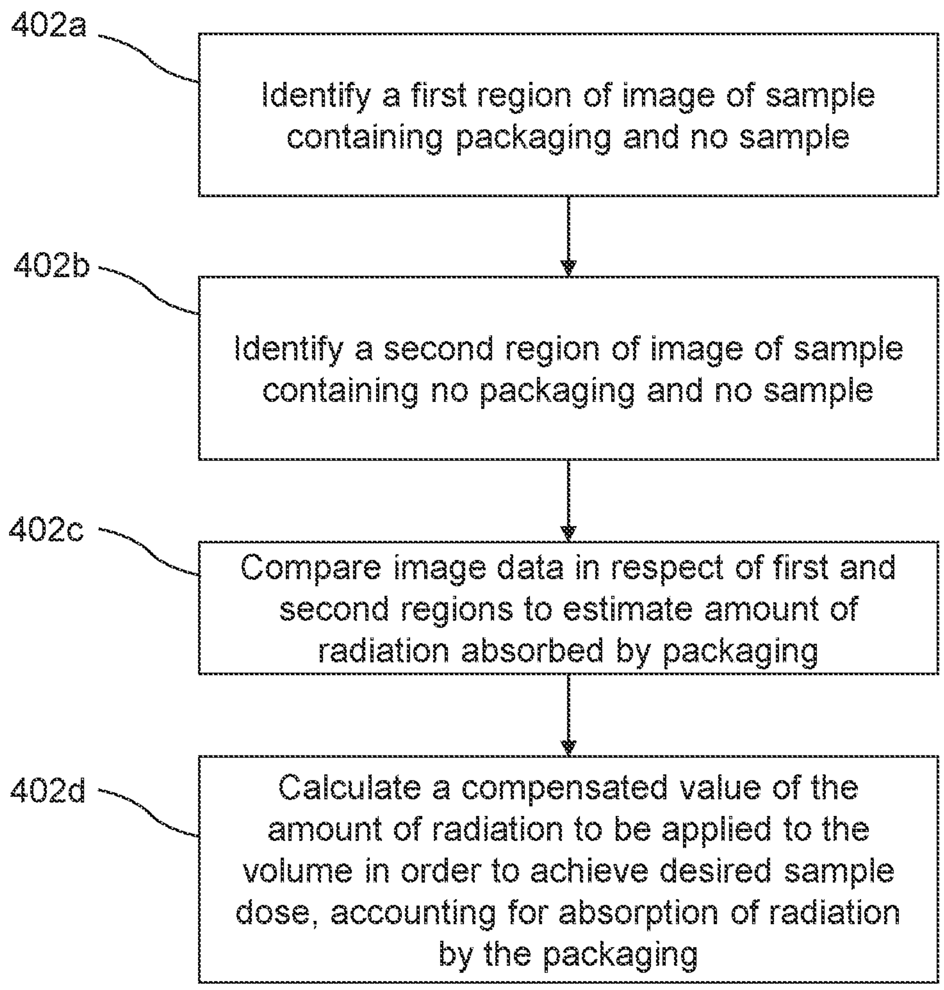

FIG. 14(*a*) shows a method of operating the irradiation apparatus. At block 402 the irradiation apparatus acquires imaging data about the samples in the irradiation volume.

At block 404 the method determines an optimum use of the radiation source points. This will be called irradiation planning data. The irradiation planning data can use one or more of the following parameters;

- a total radiation dose;
- a rate of delivering radiation;
- a total duration of the irradiation;
- a number of radiation source points activated (from 1 through to the maximum; fixed, or varying over duration of the irradiation cycle);
- radiation output by the activated radiation source points (fixed, or varying over duration of the irradiation cycle), where radiation output is determined by (i) tube current I1 to control energy per photon and (ii) tube voltage V2 to control energy per photon;
- a beam angle of each of the activated radiation source points (fixed, or varying over duration of the irradiation cycle). As described above, beam angle can be controlled by a collimator.

Figure 15:
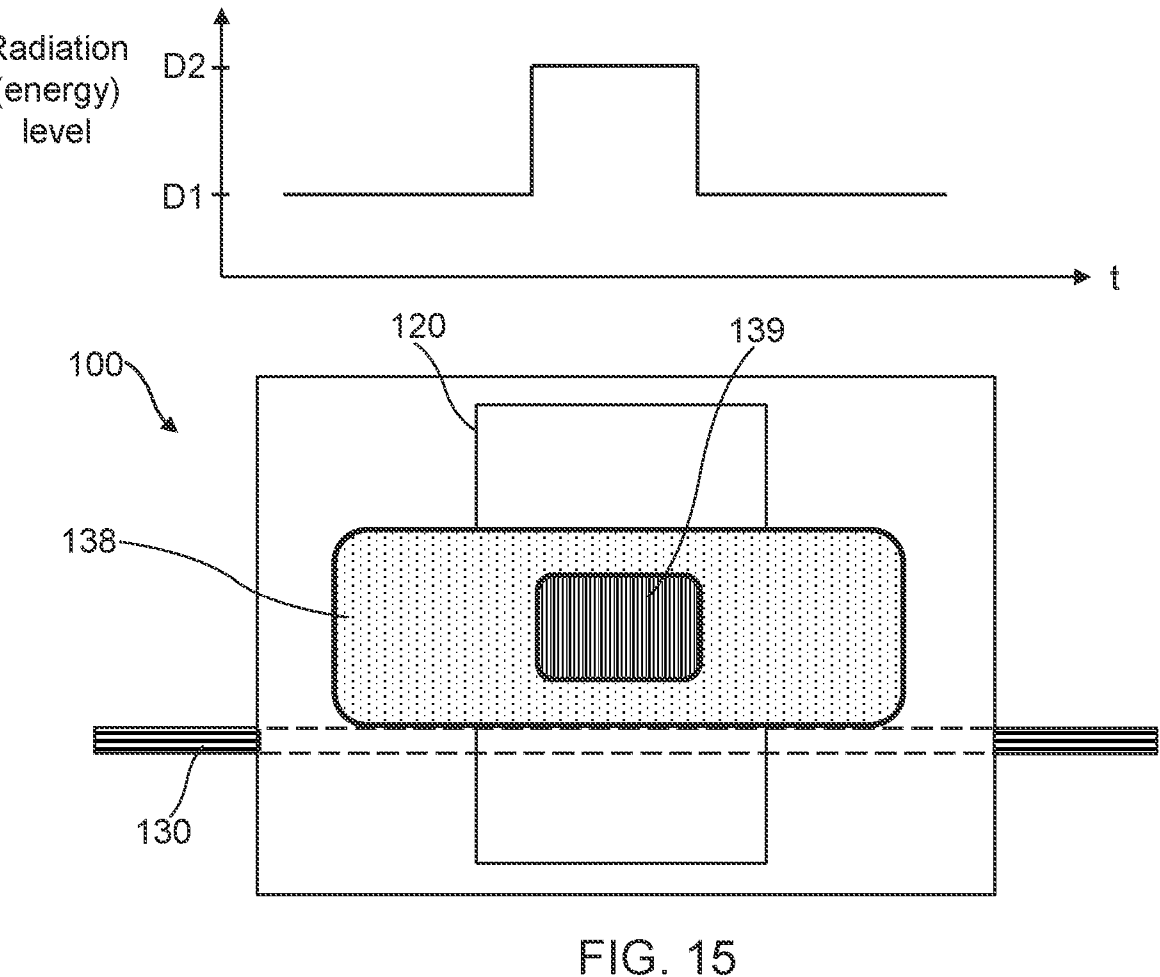
FIG. 15 shows an example of varying dose during irradiation of a sample.

The irradiation planning data may use one or more of these parameters. Each of the parameters may be fixed for the duration of the irradiation: Alternatively, it is possible to vary one or more of the parameter values during the irradiation:

Image data may indicate that one of the samples has a higher density, or a higher density region, and therefore requires a higher energy of radiation. For example, FIG. 15 shows a denser region 139 within a sample 138. The irradiation planning data can cause a radiation source point to increase radiation level when the higher density sample is nearest that radiation source point. For example, tube voltage (energy per photon) can be increased when a denser sample (or a denser region of a sample) is near to a source point: Tube voltage can be decreased for a lower density sample.

At block 406 the method irradiates the volume using the irradiation planning data.

It is to be understood that, in some embodiments, the method may require that the amount of radiation absorbed by packaging of the sample may be estimated based on acquired image data, and the amount of absorption compensated for in determining the amount of irradiation to be applied to the irradiation volume. For example, the method may involve estimating the amount of radiation absorbed by packaging of the sample by identifying:

(a) a portion of an image of the irradiation volume corresponding to a region in which the radiation has passed through packaging only, without passing through any portion of the sample, and (b) a portion of the image of the irradiation volume in which the radiation has been detected by the detector without passing through the sample or packaging.

The estimated amount of radiation absorbed by the packaging as estimated above may thus be added to the desired dose to be provided to the sample in order to estimate the amount of radiation to which the sample and packaging should be subject in order to achieve the desired dose to the sample. It is to be understood that this method may be automated in some embodiments in order to reduce user workload in calculating the required dose to be applied to the irradiation volume in which the packaged sample is provided.

FIG. 14(*b*) is a schematic illustration of an image acquired by the apparatus 100 in which a sample 138 may be seen contained within sample packaging 138*p*, in this case a bag made from a plastics film material. A suitable first region R1 of the image is shown, formed primarily by X-ray radiation that has passed through sample packaging 138*p* only and not the sample 138 (it is to be understood that a small amount of radiation may contribute to the image due to scattering by e.g. the sample 138 or portions of the apparatus 100). A suitable second region R2 of the image is also shown, formed primarily by X-ray radiation that has passed substantially directly from the X-ray source to the detector without passing through the sample 138 or sample packaging 138*p*.

FIG. 14(*c*) shows a method of calculating a packaging-compensated amount of radiation to be applied to the irradiation volume. The method may be implemented at step 302 of the method illustrated in FIG. 14(*a*).

At block 402*a* a first region R1 (FIG. 14(*b*)) of an image of a sample 138 acquired by the apparatus 100 is identified that contains an image of packaging 138*p* and no sample.

At block 402*b* a second region R2 of the image is identified that does not contain a portion of the packaging 138*p* or sample 138, but rather is formed by radiation impinging directly on the detector from the source.

At block 402*c*, image data in respect of the first and second regions R1, R2 indicative of the amount of radiation incident on the detector in those respective regions is compared in order to estimate an amount of radiation absorbed by the packaging 138*p*.

At block 402*d* a compensated value of the amount of radiation to be applied to the irradiation volume in order to achieve the desired sample dose, accounting for absorption of radiation by the packaging 138*p*, is calculated.

It is to be understood that absorption of radiation by a sample holder 134 (where present, see e.g. FIG. 17) may also be similarly compensated for. This may be achieved by estimating the amount of radiation absorbed by the sample holder 134 and packaging of the sample (where packaging is present) by identifying:

(a) a portion of an image of the irradiation volume corresponding to a region in which the radiation has passed through the sample holder and packaging only, without passing through any portion of the sample, and (b) a portion of the image of the irradiation volume in which the radiation has been detected directly by the detector without passing through the sample holder, the sample or packaging.

The method steps 402*a*-402*d* may be adjusted such that the first region of the image corresponds to a region of the irradiation volume in which radiation has passed through the sample holder 134 and sample packaging but not the sample itself, and the second region of the image corresponds to a region of the irradiation volume in which radiation has been detected directly by the detector without passing through the sample holder 134, sample packaging or the sample itself.

The radiation dose used during imaging is typically lower, or much lower, than the radiation dose used during irradiation. Radiation dose is measured using the SI unit Gray (Gy). Imaging typically uses a dose of 0.005-0.1 Gy. Irradiation typically uses a dose of at least 1 Gy but some applications can use a lower dose, such as a dose of at least 0.02 Gy. In contrast, imaging is typically in the range of 0.005-0.1 Gy.

Properties of samples transported into the irradiation apparatus can: (i) vary within one of the samples (e.g. a large bale with a damp central portion and drier outer portions, or a bale with denser region); (ii) vary from sample to sample; or (iii) be uniform (or assumed to be uniform) across a batch of samples, e.g. human plasma. The imaging and planning steps (blocks 402, 404) can be performed on a per sample basis, or on a less frequent basis. When performed on a less frequent basis, planning data from an earlier imaging operation is used unto new planning data is obtained. It is also possible to define one or more templates of parameter values for particular samples or conditions.

FIG. 15 shows an example of varying radiation level during irradiation of a sample. A sample 138 has a denser region 139. To achieve a uniform dose across the sample, the denser region 172 of the sample requires a higher radiation level. The upper part of FIG. 15 shows the radiation level delivered by radiation source 120 over a period of time. The radiation level begins at a value D1, rises to a value D2 when the denser region 172 of the sample passes through the radiation source 120, and then returns to value D2. This is a simple example. The radiation profile can have a more complicated shape, and may apply to a selected one or more of the radiation source points. A beam shape of the radiation source points may be varied to focus radiation in a particular region of the sample. The same method can be applied to an entire sample, so that a first sample is irradiated at a first radiation level and a second sample is irradiated at a second radiation level. While the energy level of the radiation delivered to a sample (or a region of a sample) is non-uniform, the overall energy level of the radiation delivered per unit volume and unit mass is more uniform.

The controller can vary a speed of the transport apparatus 130. Varying the speed of the transport apparatus 130 varies speed of linear movement of a sample through the irradiation volume 140. Reducing the speed increases the length of time that the sample (or a region of the sample) remains in the irradiation volume. Increasing the speed reduces the length of time that the sample (or a region of the sample) remains in the irradiation volume. Varying the energy level and speed can vary the radiation dose delivered to the sample (or region of the sample).

In a simpler example, where the irradiation lacks a detector array and a capability to image the irradiation volume, the irradiation apparatus can receive inputs to set parameters for an irradiation cycle such as: a total radiation dose; a rate of delivering radiation; a total duration of the irradiation; a number of radiation source points activated (from 1 through to the maximum); a power of each of the activated radiation source points; a beam angle of each of the activated radiation source points. The irradiation apparatus can determine operating parameters for the array of radiation source points 122 based on the input values. Parameters may be input to the processing apparatus, e.g. via user interface (508, FIGURE or by an input received from another apparatus.

Figure 16:
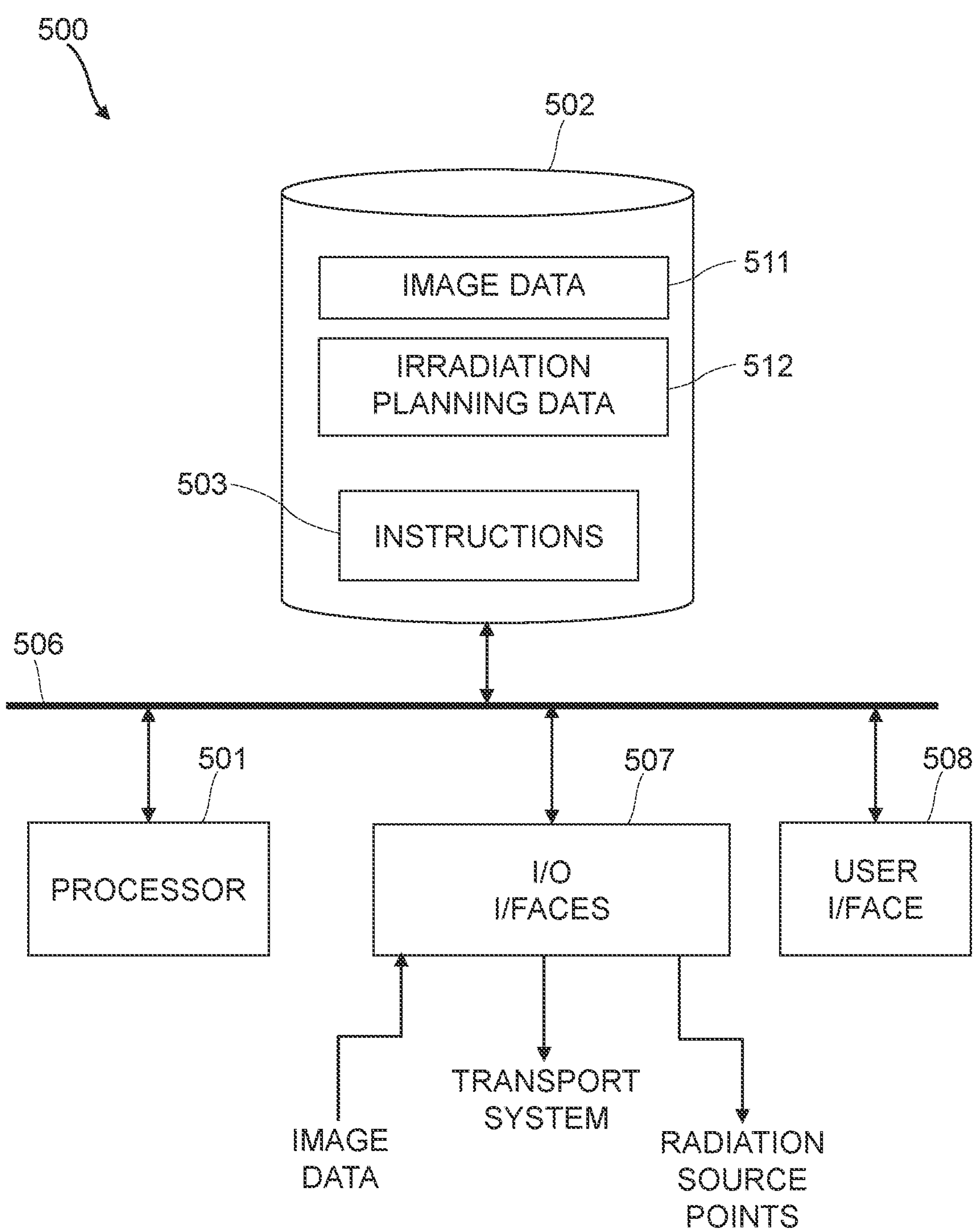
FIG. 16 shows a processing apparatus for the irradiation apparatus.

FIG. 16 shows an example of a processing apparatus 500 which may implement at least part of the processing of the invention, such as the controller 160 shown in FIG. 1. The processing apparatus 500 may implement the method of FIGS. 14(*a*) and (*c*). Processing apparatus 500 comprises one or more processor 501 which may be any type of processor for executing instructions to control the operation of the device. The processor 501 is connected to other components of the device via one or more buses 506. Processor-executable instructions 503 may be provided using any data storage device or computer-readable media, such as memory 502. The processor-executable instructions 503 comprise instructions for implementing the functionality of the described methods. The memory 502 is of any suitable type such as non-volatile memory, a magnetic or optical storage device. The processing apparatus 500 comprises input/output (I/O) interfaces 507. The I/O interfaces 507 can receive signals from the detectors and output signals to control the irradiation apparatus, e.g. control the number of radiation source points, power, beam width; control operation of the transport system (e.g. speed of linear movement). The processing apparatus 500 connects to a user interface 508. Memory 502, or a separate memory, stores data used by the processor. This can include one or more of: image data 511; irradiation planning data 512.

The dose may vary according to a type of application. Radiation dose is measured using the SI unit Gray (Gy) and dose rate in Gray/minute (Gy/min). Sterilization typically requires a high or a very high dose (e.g. 15-50 Gy dose for blood bags; 400-15,000 Gy dose for fruits, vegetables, nuts, meat, fish, poultry and animal feed; 2,500-15,000 Gy dose for *cannabis* bags/bottles). This can be delivered at a high dose rate, and may require an irradiation cycle of the order of hours, or tens of hours. Other applications can require a smaller dose, e.g. irradiation of cells for clinical research requires a dose of 0.2-25 Gy at a dose rate of 2-15 Gy/min.

Figure 17:
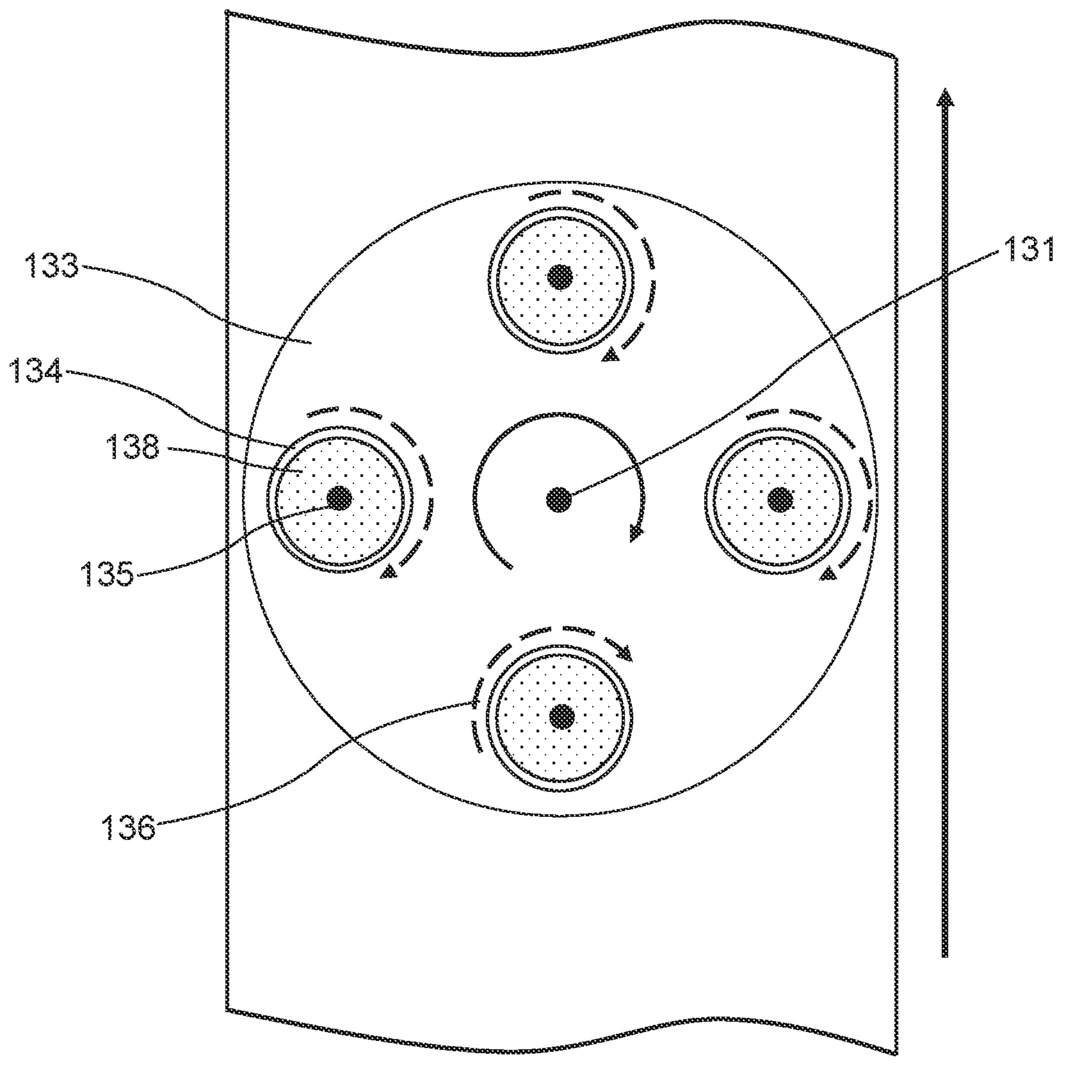
FIG. 17 shows a transport apparatus which can rotate samples.

The transport apparatus 130 described above has a conveyor belt which can transport samples along a linear path through the irradiation volume 140. FIG. 17 shows a further example of a transport apparatus which is configured to vary the position of samples during the linear path through the irradiation volume 140. For example, the transport apparatus can include a turntable 133 which is mounted on the belt.

The turntable moves with the belt. The turntable can be configured to rotate about a rotational axis. The rotational axis can be orthogonal to the linear direction of travel of the belt, i.e. upright in the example shown in FIGS. 1 and 2. As the belt moves along the linear path, the turntable rotates about the rotational axis. This varies the position of the samples on the turntable with respect to the radiation source points as the belt moves along the linear path. The turntable can comprise a plurality of holders or carriers. Each of the holders can hold a sample (e.g. an object or a quantity of material) to be irradiated in the same manner as described above for the holders on the belt.

Optionally, each of the holders 134 can also rotate about its own central axis 135. Rotation of each holder 134 is shown by the dashed arrows 136. This movement is called a double planetary. Each holder 134 rotates in direction 136 about its own axis 135 simultaneously with rotation of the entire assembly 130 about the central axis 131. In other examples, the rotational axis of a holder 134 can be eccentric. In some embodiments the sample holder 134 may be a container that substantially encapsulates a sample 138. Alternatively, the sample holder 134 may partially encapsulate a sample 138, for example the holder 134 may be open-topped. In some embodiments the sample holder 134 may be a platform upon which a sample 138 rests, optionally a sample 138 contained within sample packaging 138*p*.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An irradiation apparatus, comprising:

a shielded housing;

a plurality of ionising radiation source points configured to output ionising radiation, wherein the plurality of ionising radiation source points is a first array distributed around an irradiation volume and the first array of ionising radiation source points is configured to direct ionising radiation inwardly to the irradiation volume;

a transport apparatus configured to support at least one sample to be irradiated, wherein the transport apparatus is configured to transport samples along a linear path through the irradiation volume;

a detector array; and a controller configured to control operation of the plurality of ionising radiation source points and the detector array, wherein the controller is configured to:

image the irradiation volume using at least one of the ionising radiation source points of the first array and the detector array to acquire image data of the at least one sample within the irradiation volume; or image an imaging volume to acquire image data of the at least one sample within the imaging volume, wherein the irradiation volume is linearly offset from the imaging volume along the linear path, the irradiation apparatus comprising a second array of ionising radiation source points distributed around the imaging volume, the second array of ionising radiation source points configured to output ionising radiation, and the controller is configured to image the imaging volume using the second array of ionising radiation source points and the detector array; and irradiate the at least one sample within the irradiation volume by controlling the plurality of ionising radiation source points of the first array based on the acquired image data.

2. The irradiation apparatus according to claim 1, wherein the first array of ionising radiation source points comprises a ring of ionising radiation source points.

3. The irradiation apparatus according to claim 1, wherein the first array of ionising radiation source points comprise a plurality of rings of ionising radiation source points, wherein the rings are offset along the linear path.

4. The irradiation apparatus according to claim 1, wherein the first array of ionising radiation source points comprises a rectilinear array of ionising radiation source points.

5. The irradiation apparatus according to claim 1, wherein the linear path is orthogonal to a plane of the first array of ionising radiation source points.

6. The irradiation apparatus according to claim 1, comprising a total of N ionising radiation source points in the first array, and wherein the irradiation apparatus is configured to simultaneously activate up to N of the ionising radiation source points during an irradiation cycle.

7. The irradiation apparatus according to claim 1, wherein the controller is further configured to independently control operating parameters of each of the plurality of ionising radiation source points of the first array during an irradiation cycle.

8. The irradiation apparatus according to claim 7, wherein the operating parameters are at least one of:

an activation state of the ionising radiation source point;

an operating current and/or an operating voltage of the ionising radiation source point;

a parameter for a beam controlling device of the ionising radiation source point.

9. The irradiation apparatus according to claim 1, wherein the plurality of ionising radiation source points of the first array comprise at least one of: a plurality of individual ionising radiation sources; an ionising radiation source with a plurality of ionising radiation source points.

10. The irradiation apparatus according to claim 1, wherein the controller is further configured to operate the ionising radiation source points of the first array at a first radiation level during imaging and to operate the ionising radiation source points at a second radiation level, higher than the first radiation level, during irradiation.

11. The irradiation apparatus according to claim 10, wherein the first radiation level is a dose less than 0.1 Gy.

12. The irradiation apparatus according to claim 1, wherein the controller is further configured to image the irradiation volume by:

activating different ones of the ionising radiation source points of the first array to emit a beam of radiation for imaging; and using the detector array to acquire image data.

13. The irradiation apparatus according to claim 12, wherein the controller is further configured to use the acquired image data to construct a three-dimensional image.

14. The irradiation apparatus according to claim 1, wherein the controller is further configured to control the plurality of ionising radiation source points of the first array based on the acquired image data.

15. The irradiation apparatus according to claim 1, wherein the controller is further configured to image the irradiation volume by:

activating different ones of the ionising radiation source points of the second array to emit a beam of radiation for imaging; and using the detector array to acquire image data.

16. The irradiation apparatus according to claim 15, wherein the controller is further configured to use the acquired image data to construct a three-dimensional image.

17. The irradiation apparatus according to claim 1, wherein the controller is further configured to control the plurality of ionising radiation source points of the first array based on the acquired image data.

18. The irradiation apparatus according to claim 1, wherein the controller is further configured to determine data indicative of density of a sample within the irradiation volume based on the acquired image data.

19. The irradiation apparatus according to claim 1, wherein the controller is further configured to determine data indicative of volumetric and/or spatial distribution of a sample within the irradiation volume based on the acquired image data.

20. The irradiation apparatus according to claim 1, wherein the controller is further configured to determine a required amount of irradiation to which a sample is to be subject based on the acquired image data and to control the plurality of ionising radiation source points of the first array to deliver the required amount.

21. The irradiation apparatus according to claim 20, wherein the controller is further configured to control the plurality of ionising radiation source points of the first array to deliver the required amount of radiation taking into account the presence of a sample holder and/or sample packaging.

22. The irradiation apparatus according to claim 1, wherein the controller is further configured to determine at least one of:

a number of ionising radiation source points of the first array to be activated;

an operating current and/or an operating voltage of the activated ionising radiation source points of the first array;

a parameter for a beam controlling device at an ionising radiation source point of the first array;

a total duration of the irradiation.

23. The irradiation apparatus according to claim 1, wherein the transport apparatus comprises a conveyor belt.

24. The irradiation apparatus according to claim 1, wherein the transport apparatus is configured to vary a speed at which samples are moved along the linear path by the transport apparatus.

25. The irradiation apparatus according to claim 1, wherein the transport apparatus is configured to vary a position of samples during the linear path through the irradiation volume.

26. The irradiation apparatus according to claim 1, wherein the ionising radiation is X-ray radiation.

27. A method of irradiating at least one sample by the irradiation apparatus of claim 1, the method comprising:

supporting the at least one sample within the irradiation volume and transporting the at least one sample along a linear path through the irradiation volume;

imaging the irradiation volume using at least some of the ionising radiation source points of the first array and the detector array to acquire image data of the at least one sample within the irradiation volume; or imaging an imaging volume using a second array of ionising radiation source points distributed around the imaging volume and the detector array to acquire image data of the at least one sample within the imaging volume, wherein the second array of ionising radiation source points output ionising radiation, wherein the irradiation volume is linearly offset from the imaging volume along the linear path; and irradiating the at least one sample within the irradiation volume by controlling the plurality of ionising radiation source points of the first array based on the acquired image data.

28. The method according to claim 27, wherein there is a total of N ionising radiation source points in the first array, and wherein the method further comprises selecting a number up to N of the ionising radiation source points to simultaneously activate during an irradiation cycle.

29. The method according to claim 27, further comprising independently controlling operating parameters of each of the plurality of ionising radiation source points of the first array during an irradiation cycle.

30. The method according to claim 29, wherein the operating parameters are at least one of:

an activation state (on/off) of the ionising radiation source point;

an operating current and/or an operating voltage of the ionising radiation source point;

a parameter for a beam controlling device of the ionising radiation source point.

* * * * *